United States Patent
Taylor et al.

(10) Patent No.: US 10,781,419 B2
(45) Date of Patent: Sep. 22, 2020

(54) MOSQUITO SALIVARY GLAND EXTRACTION DEVICE AND METHODS OF USE

(71) Applicants: Sanaria Inc., Rockville, MD (US); Johns Hopkins University, Baltimore, MD (US)

(72) Inventors: Russell H. Taylor, Severna Park, MD (US); Amanda Canezin, Newton, MA (US); Mariah Schrum, Jefferson Hills, PA (US); Iulian Iordachita, Lutherville, MD (US); Gregory Chirikjian, Towson, MD (US); Michelle Laskowski, Frederick, MD (US); Sumana Chakravarty, Derwood, MD (US); Stephen Hoffman, Gaithersburg, MD (US)

(73) Assignees: Sanaria Inc., Rockville, MD (US); Johns Hopkins University, Baltimore, MD (US)

( * ) Notice: Subject to any disclaimer, the term of this patent is extended or adjusted under 35 U.S.C. 154(b) by 342 days.

(21) Appl. No.: 15/621,875

(22) Filed: Jun. 13, 2017

(65) Prior Publication Data
US 2017/0355951 A1  Dec. 14, 2017

Related U.S. Application Data

(60) Provisional application No. 62/349,555, filed on Jun. 13, 2016.

(51) Int. Cl.
*B01L 9/00* (2006.01)
*C12N 3/00* (2006.01)
*C12N 1/10* (2006.01)
*C12M 1/00* (2006.01)

(52) U.S. Cl.
CPC ............... *C12N 3/00* (2013.01); *C12M 47/04* (2013.01); *C12N 1/10* (2013.01)

(58) Field of Classification Search
CPC ....... B01L 2200/025; B01L 2300/0609; B01L 2400/0481; B01L 9/00
USPC .......................................... 422/560, 554, 566
See application file for complete search history.

(56) References Cited

U.S. PATENT DOCUMENTS

2004/0006873 A1 *  1/2004  Cutting .................. B26B 19/06 30/133

OTHER PUBLICATIONS

Borchers, C., "Robot may help fight malaria ," Bostonglobe.com, May 8, 2014, accessed at http://www.bostonglobe.com/business/2014/05/07/mosquito-harvest/Qxto58qtpGHhRVfliT6aHI/story.html, accessed on Jun. 13, 2017, 8 pages.
Brown, A.E., et al., "Toward silencing the burden of malaria: progress and prospects for RNAi-based approaches," *BioTechniques* 40:S38-S44 (2006).

(Continued)

*Primary Examiner* — Natalia Levkovich
(74) *Attorney, Agent, or Firm* — Sterne, Kessler, Goldstein & Fox P.L.L.C.

(57) ABSTRACT

A device and method of use for augmenting the extraction of salivary glands from *Plasmodium*-infected mosquitoes, where the sporozoite stage of *Plasmodium* primarily resides. Sporozoites are useful for research as well as for the immunogen in whole parasite vaccines for the prevention of malaria. The device and methods of use disclosed herein greatly increase the rate at which sporozoites can be harvested.

14 Claims, 32 Drawing Sheets

(56) References Cited

OTHER PUBLICATIONS

Laposwky, I., "The Next Big Thing You Missed; This Mosquito-Dissecting, Malaria-Killing Robot Needs your Help," Wired.com, Jun. 3, 2014, accessed at https://www.wired.com/2014/06/the-next-big-thing-you-missed-a-crowdfunded-mosquito-dissecting-malaria-killing-robot, accessed on Jun. 12, 2017, 5 pages.

Richie, T.L., et al., "Progress with *Plasmodium falciparum* sporozite (PfSPZ)-based malaria vaccine," *Vaccine* 33:7452-7461, Elsevier, United States (2015).

"Malaria," cdc.gov, accessed at https://www.cdc.gov/malaria, accessed on Jun. 12, 2017, 2 pages.

"Mosquito-borne disease," Wikipedia.com, accessed at https://en.wikipedia.org/wiki/Mosquito-borne_disease, accessed on Jun. 12, 2017, 4 pages.

Sanaria Inc. "SporoBot—Build a Robot. Fight Malaria. Save Lives!," YouTube.com, published May 5, 2014, accessed at https://www.youtube.com/watch?feature=player_embedded&v=VblazNXcHFg, accessed on Jun. 12, 2017, 2 pages.

\* cited by examiner

MOSQUITO SALIVARY GLAND EXTRACTION DEVICE AND METHODS OF USE

CROSS-REFERENCE TO RELATED APPLICATIONS AND INCORPORATION BY REFERENCE

This non-provisional application claims priority to U.S. Provisional Application No. 62/349,555, filed Jun. 13, 2016, which is incorporated herein by reference in its entirety for all purposes.

STATEMENT REGARDING FEDERALLY-SPONSORED RESEARCH AND DEVELOPMENT

This invention was made with government support under Contract No. W911QY15C0076 awarded by the Natick Contracting Division, U.S. Army Contracting Command—APG; and with government support under Grant No. 1R43AI112165-01 awarded by NIH National Institute of Allergy and Infectious Diseases. The government has certain rights in the invention.

FIELD OF THE INVENTION

This invention relates generally to dissection of mosquitoes, to malaria, and to whole parasite malaria vaccines.

BACKGROUND

Mosquito-borne diseases such as malaria and yellow fever are among the most serious challenges to public health world-wide, affecting over 700 million people per year [1]. The Centers for Disease Control estimates that there were 198 million cases of malaria worldwide in 2013, with 500,000 deaths [3]. Development of vaccines against these dread diseases is a significant public health priority.

Human malaria is an infectious disease vectored by *Plasmodium*-species parasites and transmitted to humans from *Anopheles* mosquitoes by the "sporozoite" developmental stage of the parasite. Plasmodia are indirect parasites with sexual stages occurring in the mosquito, and asexual (disease-causing) stages in the intermediate host. The sporozoite is the developmental stage of Plasmodia that resides in mosquito salivary glands immediately prior to passage to the animal or human host during feeding (FIG. 1). Presently there is no licensed vaccine for the prevention of malaria. Promising approaches, developed by Sanaria Incorporated, Rockville, Md., involve the use of *Plasmodium* sporozoites as immunogens in live, whole parasite vaccines [7]. These vaccines are showing substantial promise clinically, and their safety and high-level efficacy will make them ideal for large-scale malaria elimination campaigns in geographically define malarious regions. However, a limitation in the production of sufficient quantities of vaccine for elimination campaigns is the extraction of the salivary glands and isolation of sporozoites from large numbers of infected mosquitoes.

FIG. 2 shows a diagram of the mosquito 10. The salivary glands are located in the thorax region 11 of the mosquito body. Currently, the process of salivary gland extrusion, extraction, and sporozoite isolation is completely manual, and consists of the following steps:

1. A quantity of infected mosquitoes is placed in a small dish under a microscope;
2. A technician grasps a mosquito 10 with tweezers and separates it from the others;
3. The technician then uses the sharp edge of a hypodermic needle to cut the head 12 off the mosquito at the neck 13;
4. The technician then gently squeezes the body of the mosquito to extrude the salivary gland from the thorax 11; and
5. The technician then uses the hypodermic needle to suction up the salivary gland and transfers it to a collection container.

In some cases, the salivary gland remains with the head when it is removed. In these cases, the technician removes the gland from the head and then uses the hypodermic needle to suction it up and transfers it to the container, as before.

The overall throughput for one technician appears to be about 5-6 mosquitoes per minute (equivalent to >500,000 sporozoites per minute), though this rate may increase somewhat with experience. While this method is capable of producing sufficient sporozoites for the vaccine regimens required for clinical trials, it would be useful to augment the procedure for salivary gland extraction and sporozoite production to reduce the cost of goods, increase the rate of vaccine production and ensure the manufacture of sufficient vaccine regimens for post-licensure elimination campaigns.

There has been at least one effort to fully automate the sporozoite production process by means of a robot [4]. There was a You Tube promotional video included as part of a fund-raising effort [5] and a newspaper article [6], but the robot was never completed. The process included a computer vision system to locate mosquitoes in a dish and a Cartesian (XYZ) robot to position an end effector that would grasp the mosquito and feed each one serially and sequentially into a tube for further processing. A limitation of the process as conceived [6] was that each mosquito was intended to be processed sequentially on a per-mosquito basis. A second limitation was that the cost of such a machine, if it were ever built, was anticipated to be very high. That meant that more machines than needed for production would have had to be built and purchased so that, if the one machine had to be withdrawn for repair or maintenance, production would not be negatively impacted. Thus, there is a need to augment, semi-automate or automate the procedure for salivary gland extraction and sporozoite production.

SUMMARY

The devices described in this disclosure can significantly improve the productivity of human workers in extraction of salivary glands, while lowering per-mosquito costs and improving overall process robustness. Additionally, the experience gained with use of these devices can be useful to facilitate development of more automated solutions as the demand for larger volumes of mosquito processing increases.

Disclosed herein are devices configured for augmenting the extraction of salivary glands from a multiplicity of mosquitoes comprising: a) a cartridge comprising a first end, and a second end opposite the first end and a front edge extending between the first and second ends, the cartridge additionally comprising a multiplicity of slots with a given depth arranged between the first end and the second end and the long axes of the slots being perpendicular to the front edge, each slot having an open leading end proximate to the front edge and an open trailing end distal from the front edge, the cartridge being configured to receive the multiplicity of mosquitoes, each mosquito comprising a body (which comprises a thorax), a neck and a head and the multiplicity having an average thickness, such that the multiplicity of mosquitoes can be positioned in parallel with one another, each in one of the multiplicity of slots within the cartridge such that the head of each mosquito is positioned to protrude beyond the front edge; (b) a cutting assembly comprising a first blade extending between the first end and the second end of the cartridge and configured such that the first blade can move along the front edge of the cartridge, separating the heads from the bodies of the multiplicity of mosquitoes; (c) a body squeezer or body squeezing assembly comprising a block extending between the first end and the second end of the cartridge and configured such that the block can operably be pressed to impinge upon the bodies of the multiplicity of mosquitoes, thereby extruding mosquito salivary glands from the multiplicity of mosquito bodies; and (d) a means for collecting the salivary glands. In this regard, the salivary glands from a multiplicity of mosquitoes may be extracted.

Also disclosed are methods of extracting salivary glands from a multiplicity of mosquitoes comprising: (a) placing the multiplicity of mosquitoes on a mosquito staging platform, each mosquito comprising a body (which comprises a thorax), a neck, and a head; (b) moving each mosquito into a slot in the cartridge, the cartridge having a first end, a second end opposite the first end, and a front edge extending between the first and second ends, and additionally comprising a multiplicity of slots with a given depth and arranged between the first end and the second end and the long axes of the slots being perpendicular to the front edge, each slot having an open leading end proximate to the front edge and an open trailing end distal from the front edge, each mosquito being moved into a slot such that the multiplicity of mosquitoes being arranged in parallel with one another within the slots and the heads and neck protruding beyond the open leading ends of the slots at the front edge of the cartridge; (c) passing a blade extending between the first end and the second end of the cartridge along the front edge of the cartridge, separating the heads from the bodies of the multiplicity of mosquitoes; (d) positioning a mosquito body squeezer comprising a block and extending between the first end and the second end of the cartridge, pressing upon the squeezer such that the squeezer impinges upon the bodies of the multiplicity of the mosquitoes, thereby extruding mosquito salivary glands from the multiplicity of mosquito bodies; and (e) collecting and pooling the extruded salivary glands.

DESCRIPTION OF THE DRAWINGS

FIG. 3A is a top view and FIG. 3B is in perspective.

FIG. 6A is a top view and FIG. 6B is a side view.

FIG. 7A is a top view and FIG. 7B is a front view prepared to receive intact mosquitoes. FIG. 7C is a top view and FIG. 7D is a front view of an activated (displaced blades) assembly decapitating mosquito heads.

FIG. 8A is a top view and FIG. 8B is a side view.

FIG. 9A is a top view and FIG. 9B is a side view.

FIG. 10A is a side view and FIG. 10B is a top view.

FIG. 13A is a top view and FIG. 13B is in perspective.

DETAILED DESCRIPTION

Definitions

Figure 1:
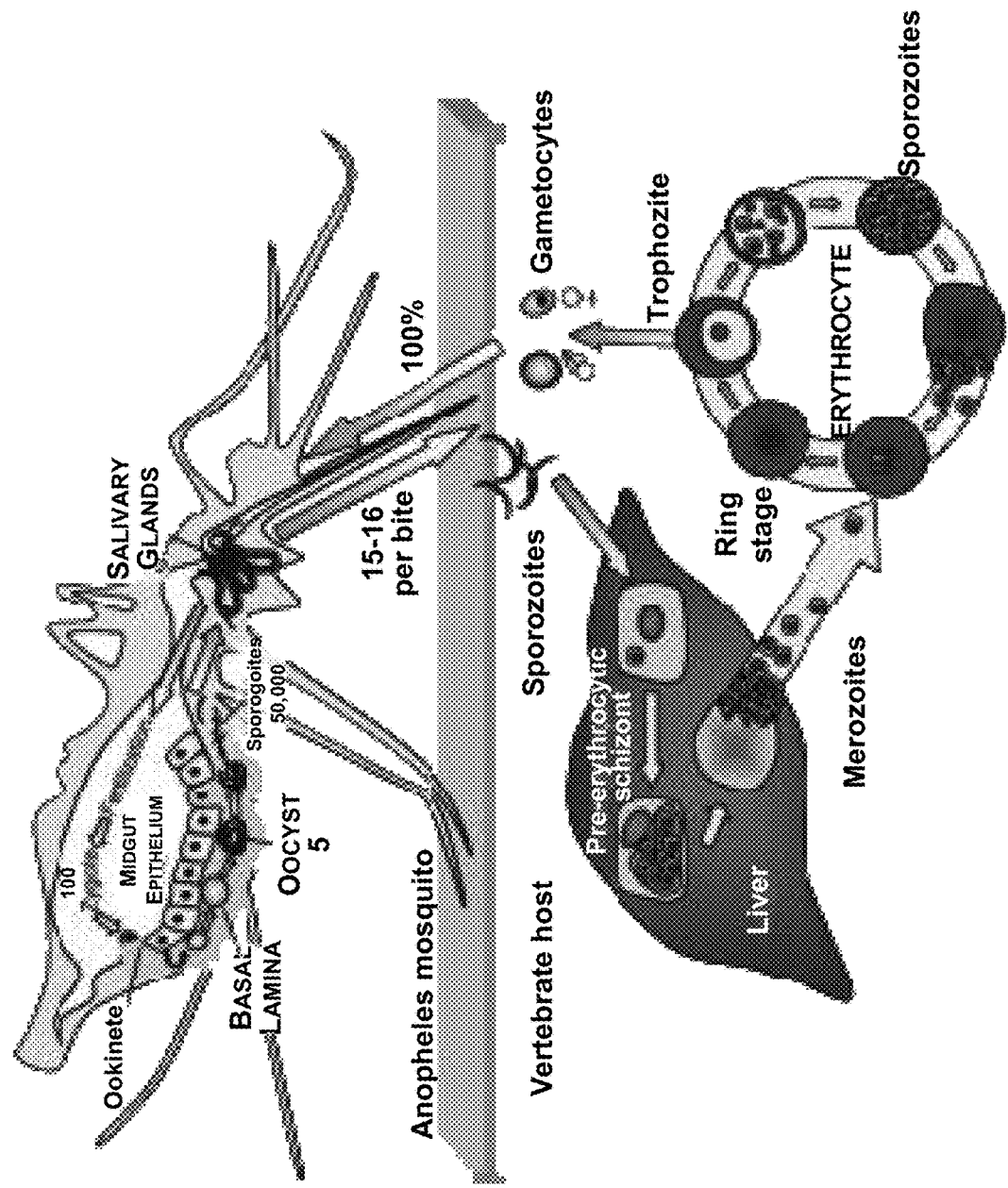
FIG. 1 depicts the life cycle of *Plasmodium* parasite, and the location of salivary glands within the mosquito thorax.
Figure 2:
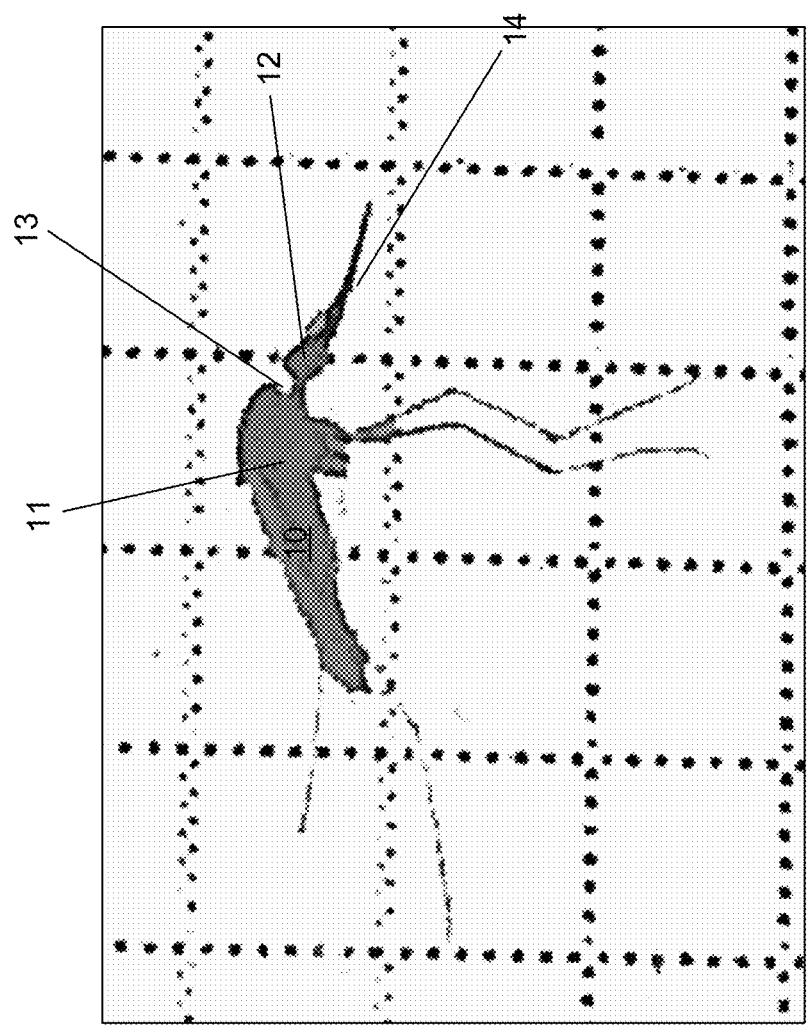
FIG. 2 depicts the gross anatomy of a mosquito. The squares represent 0.25 cm.

As defined herein, a slot is a narrow cavity open at each end of the cavity and passing from the front edge of a block or cartridge to the back edge.

As defined herein, positioned means placed in a specific position and orientation.

As defined herein, serrate or serration means an edge with a row of alternating teeth and notches.

As defined herein, a tooth is a projection between two notches in a serration.

As defined herein, a notch is an indent between two teeth in a serration.

As defined herein, a mosquito thorax is the superior segment of the mosquito body comprising the salivary glands.

Apparatus Design

The device disclosed herein is comprised of several functional elements, including: a) a cartridge with slots 20 designed to receive intact mosquitoes such that when the slots of the cartridge are loaded with a multiplicity mosquitoes, the mosquitoes are positioned, one per slot, in parallel in the loaded cartridge; b) a cutting assembly 40 comprising a blade or blade pair 70 for simultaneously or sequentially decapitating all mosquitoes in the loaded cartridge, and a mosquito body-squeezer or squeezer block 50 designed to simultaneously squeeze the thoraces of the decapitated mosquito bodies in the loaded cartridge, thereby extruding the salivary glands from all the mosquitoes in the cartridge. In some embodiments the device additionally comprises a receptacle 60 into which all the extruded salivary glands are collected. In some embodiments the device additionally comprises a mosquito staging platform 30 designed to receive a multiplicity of randomly oriented mosquitoes and from which mosquitoes can be moved into cartridge slots in appropriate positions. In some embodiments, the device comprises a platform 79 for collecting decapitated mosquito heads.

Figure 4A:
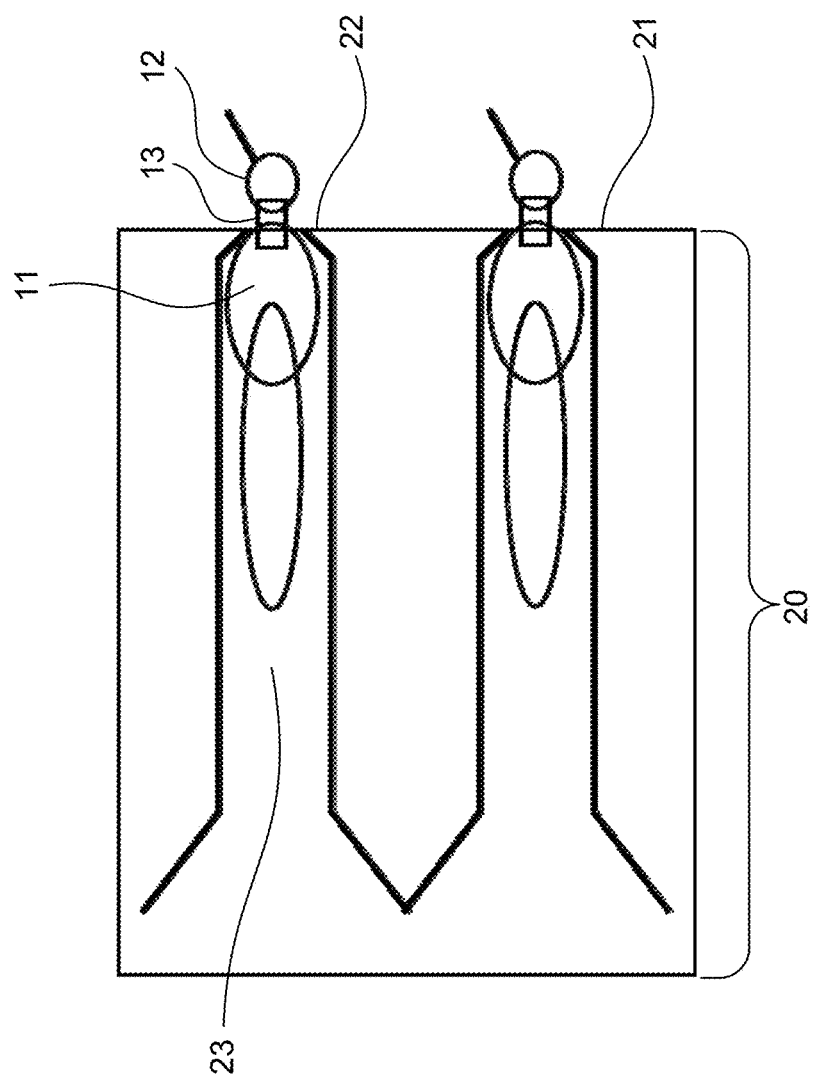
FIG. 4A depicts a top view detail of a cartridge showing slots containing mosquitoes.
Figure 4B:
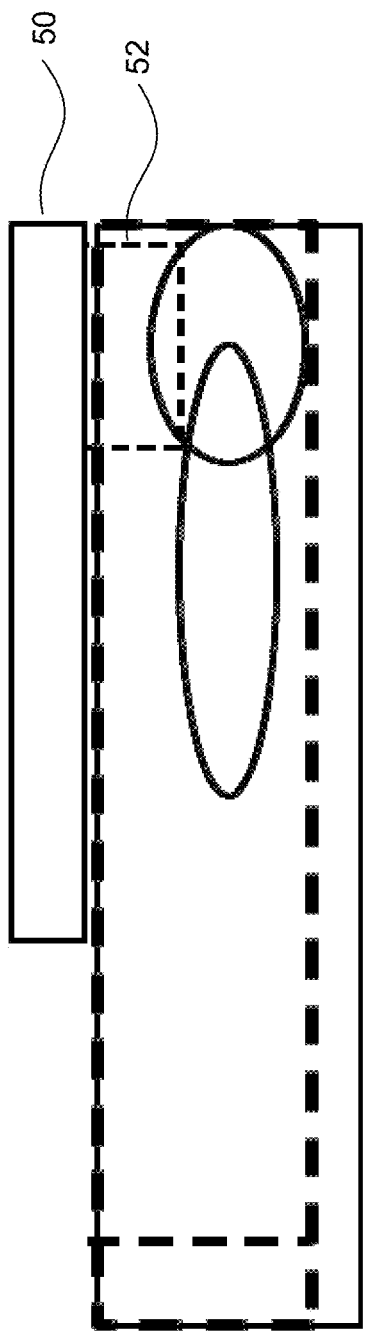
FIGS. 4B and 4C depict side view details of two embodiments of a body squeezing assembly.
Figure 4C:
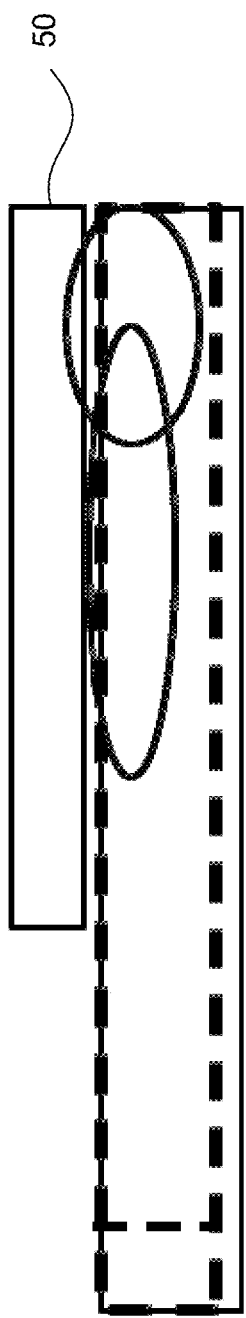

FIGS. 4A-4B show details of a cartridge design that aligns all the necks 13 of a multiplicity of mosquitoes at the front edge 21 of the cartridge so that the heads 12 can be cut off simultaneously or sequentially (as by a shearing guillotine) by means of a thin blade 70. In an embodiment, this is accomplished by a means for constricting 22 each slot 23 at the front edge 21 of the cartridge 20 such that mosquito head 12 passes through the constriction but the mosquito thorax 11 and body are constrained within the slot 23, and all the thoraces and mosquito bodies are aligned and exposed such that the salivary glands may be extruded by means of a body squeezing assembly 50 and collected simultaneously. One convenient way to arrange this is to align all the mosquitoes in parallel so that their heads protrude beyond the front edge 21 of the cartridge and their necks 13 line up beyond the edge of the cartridge. With regard to the slots 23 in a cartridge, a multiplicity means 2-150 slots, 5-50 slots, 10-40 slots, or 10-30 slots.

Figure 3A:
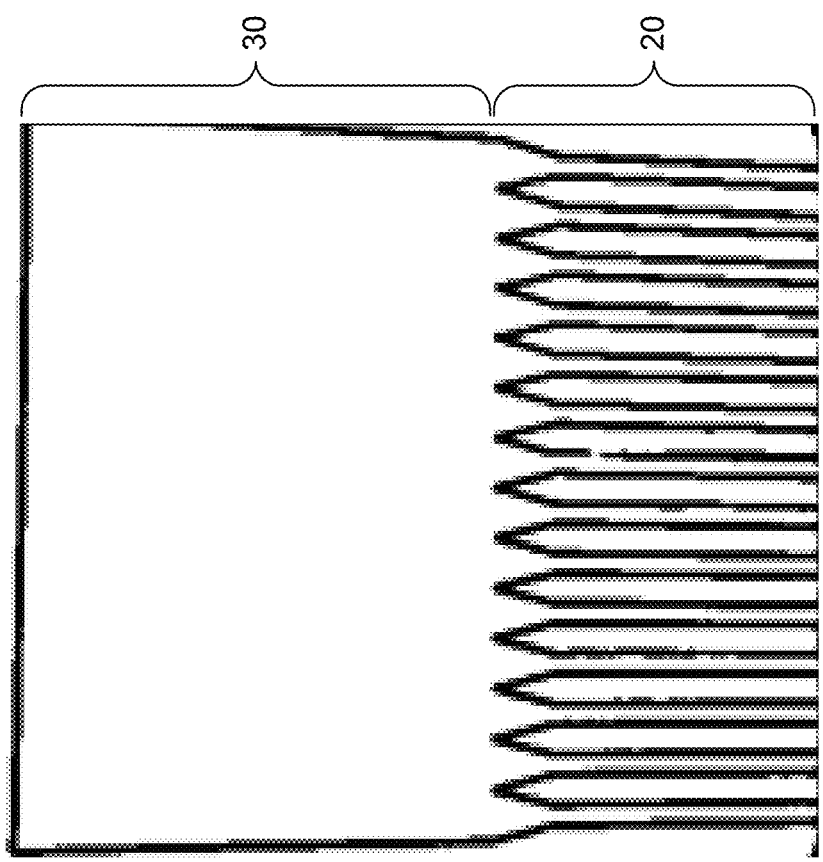
FIGS. 3A-3B depict an integrated cartridge and staging area.
Figure 3B:
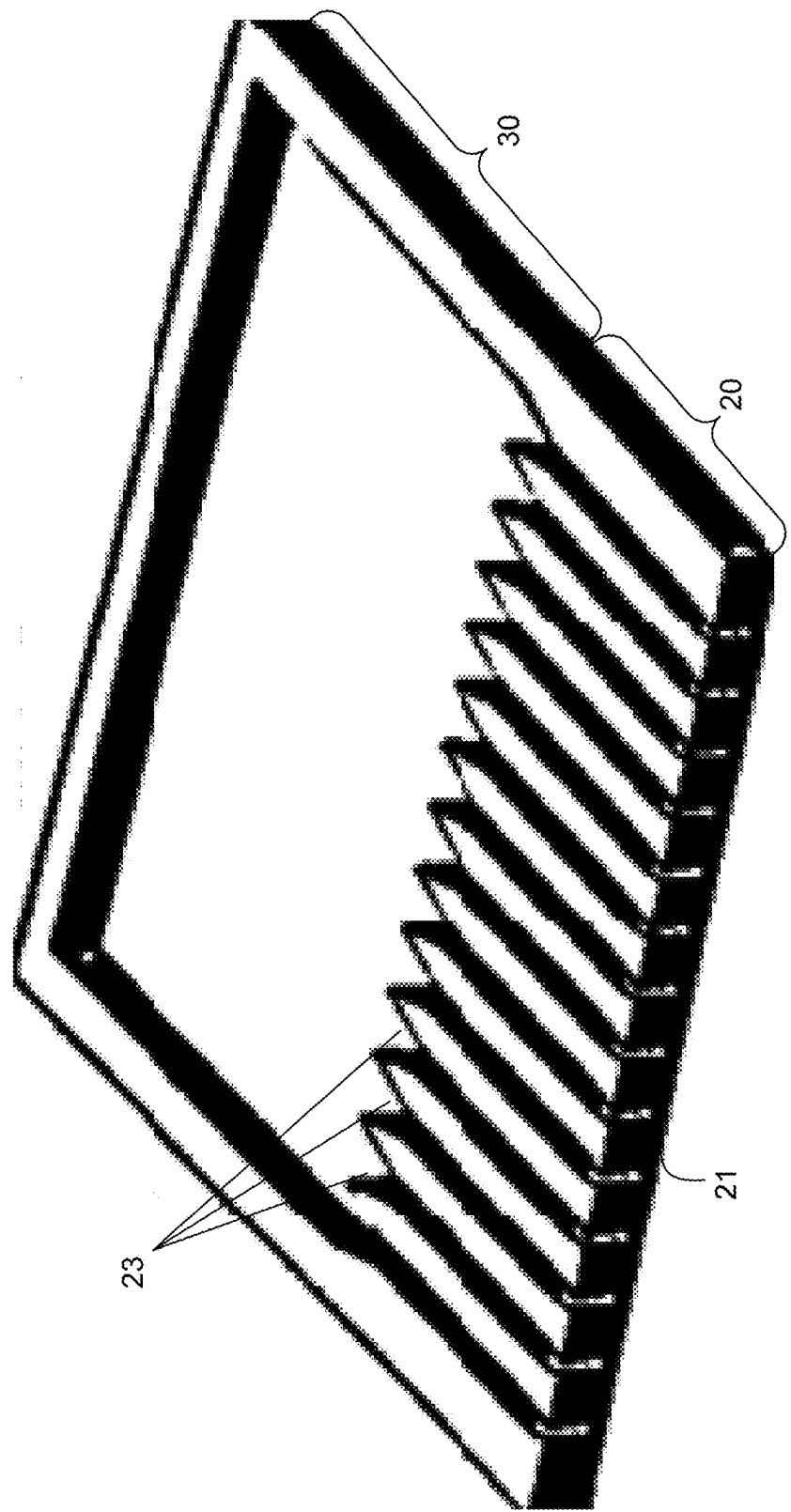

An embodiment staging platform 30 and cartridge 20 design is illustrated in FIGS. 3A-3B in which the staging platform and cartridge are an integrated unit. It comprises a central staging area 30 into which mosquitoes may be placed and a multiplicity of slots 23 leading from the staging area to the front edge 21 of the cartridge. The slots are wide enough to accommodate the body of one mosquito. It is not necessary that the fit be very tight, but should provide reasonable alignment of the mosquito body along the slot. In the embodiment shown, the end of the slot toward the staging area is chamfered to facilitate easy introduction of a mosquito into the slot. In the embodiment shown in FIGS. 4A-4B, the front edge of the slot 21 is constricted sufficiently to prevent passage of the body and thorax 11 of the mosquito but is wide enough for the head 12 of the mosquito to pass through. In other embodiments, the sides of the slots are straight and the constriction is provided by notches in the cutting assembly that abuts the slots.

Figure 5:
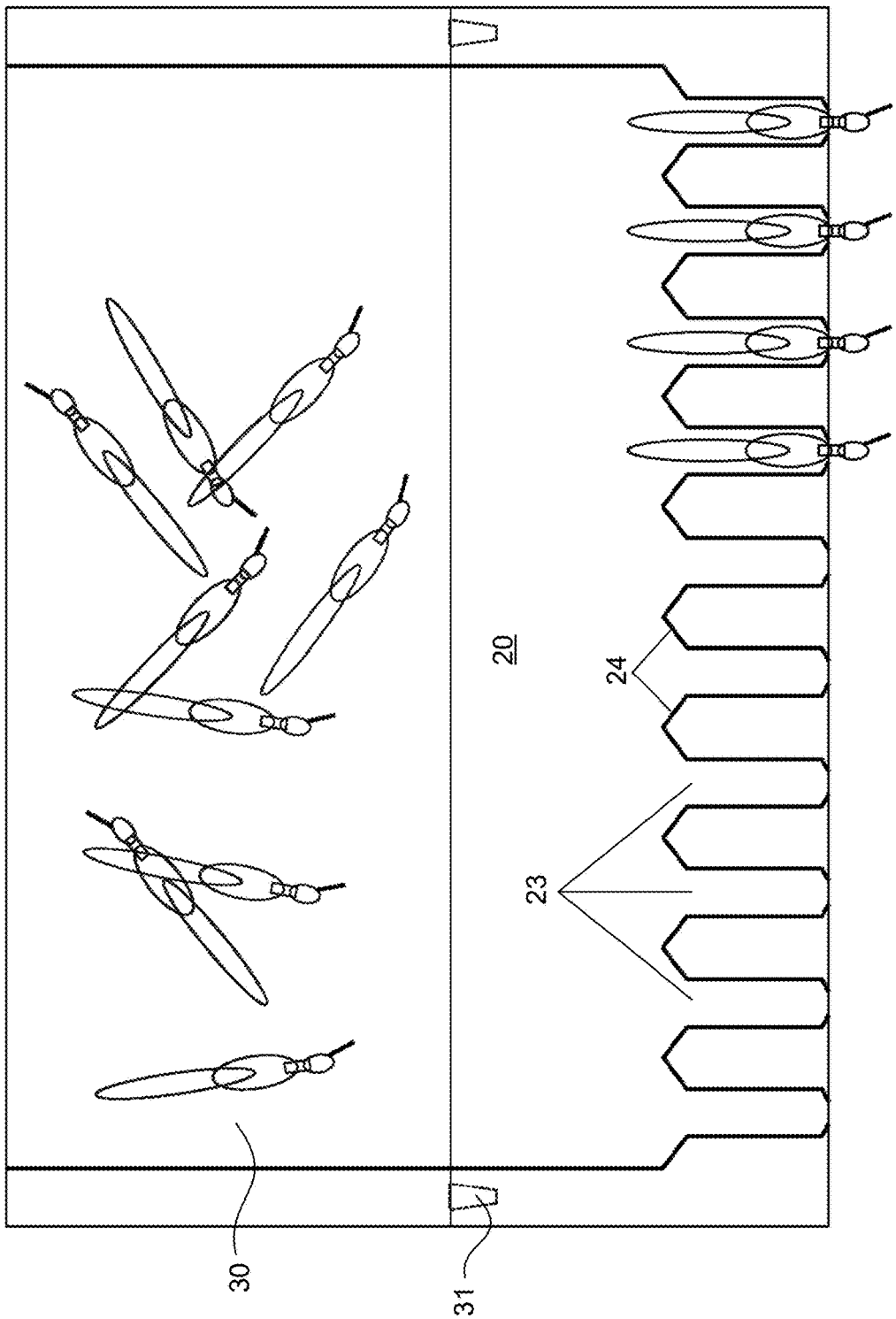
FIG. 5 depicts a cartridge detachably affixed to a staging area, as well as mosquitoes.

FIG. 5 shows an embodiment of the mosquito cartridge in which the cartridge 20 is attached or detached from the staging area 30. In this embodiment, aligning pins 31 or other means known in the art may be used to maintain the alignment of the cartridge with the staging area so as to provide a smooth surface across which to drag the mosquitoes. Spring clips with detents or similar means may be used to hold the cartridge in place relative to the staging area while mosquitoes are placed into slots. Note that the lateral alignment of the cartridge relative to the staging area is not critical, so that the aligning pins may not be needed. A simple slot or other aligning means that holds the cartridge next to the staging area may be sufficient in some embodiments. One advantage of a design in which cartridges are separable from the staging area is that the number of mosquitoes in the staging area does not need to coincide with the number of slots in the cartridge. Any convenient means may be used to deliver mosquitoes to the staging area and to spread them out enough so that it is convenient to grasp individual mosquitoes. This may be done either manually or by an automated delivery mechanism. When a cartridge is full, it may be removed and replaced by an empty one. Similarly, when the staging area is empty it may be replenished, or it may be continually replenished.

Note also that in the embodiment shown in FIG. 5, the slots are somewhat shorter than those shown in FIGS. 3A-3B and 4A-4C. As mentioned earlier, the specific length of the slots is not critical so long as the mosquito heads go through the slot openings in the cartridge edge and the thoraces are well enough constrained so that the salivary glands can be squeezed out. In this embodiment, a chamfer 24 is provided at the back end of each slot to facilitate loading of mosquitoes.

Figure 6A:
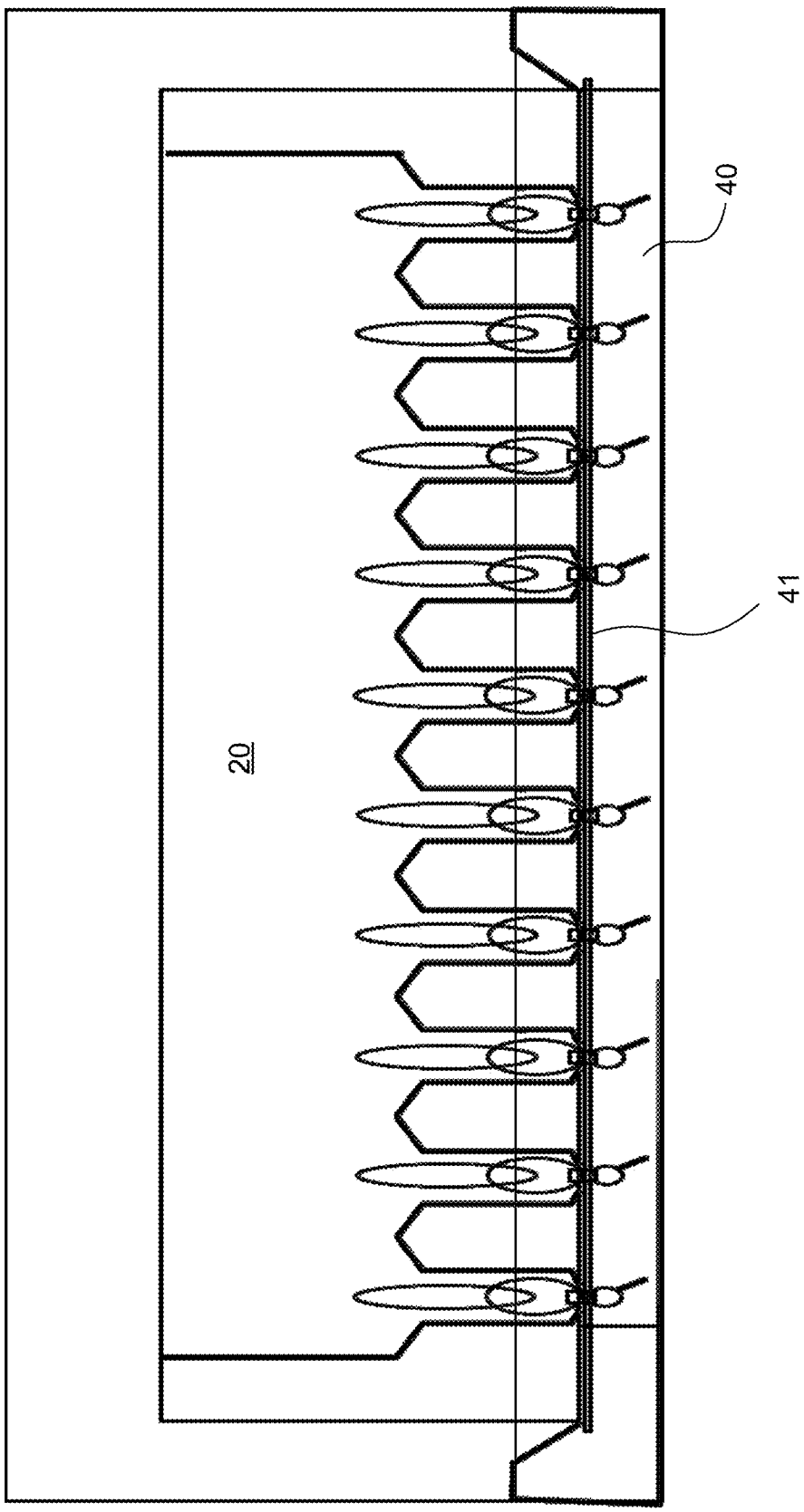
FIGS. 6A-6B depict a cartridge positioned within a cutting assembly (e.g., decapitation assembly).
Figure 6B:
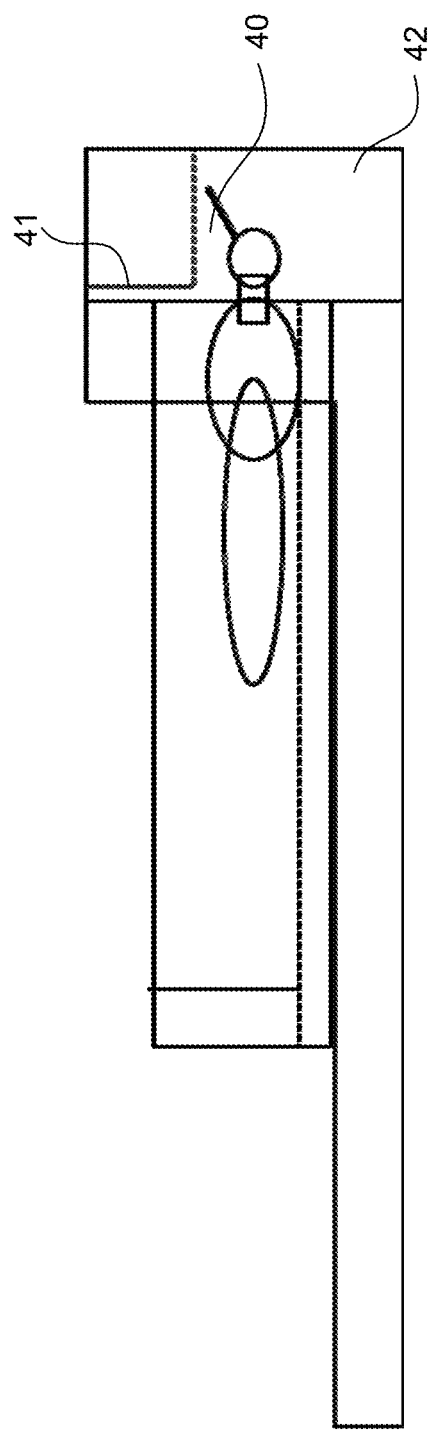
Figure 15:
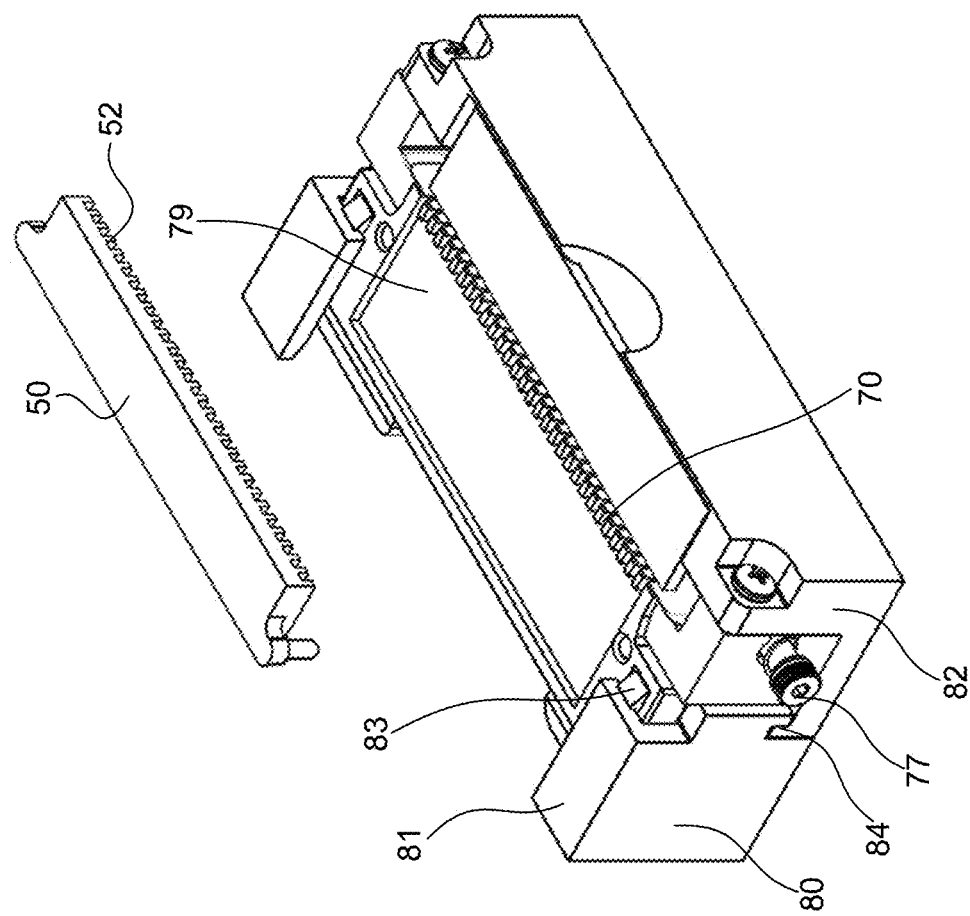
FIG. 15 is a view of the assembled rear and front bases, the cutting assembly, slotted cartridge, and slide with the squeezer above the cartridge.
Figure 16A:
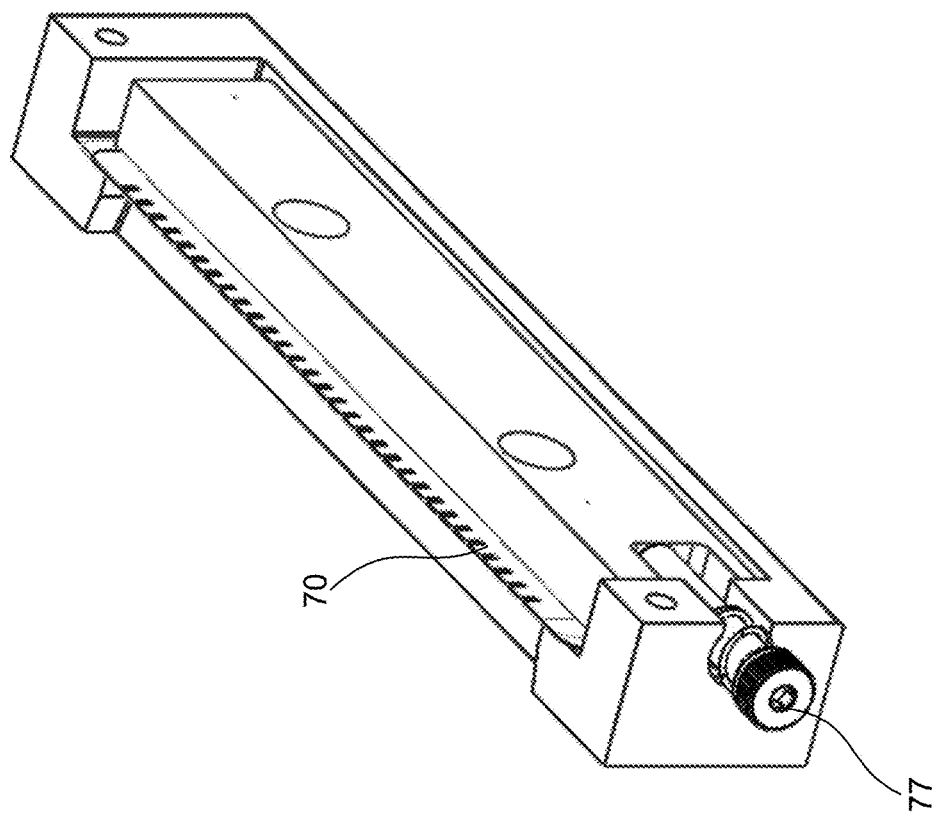
FIG. 16A shows the cutting assembly.
Figure 16B:
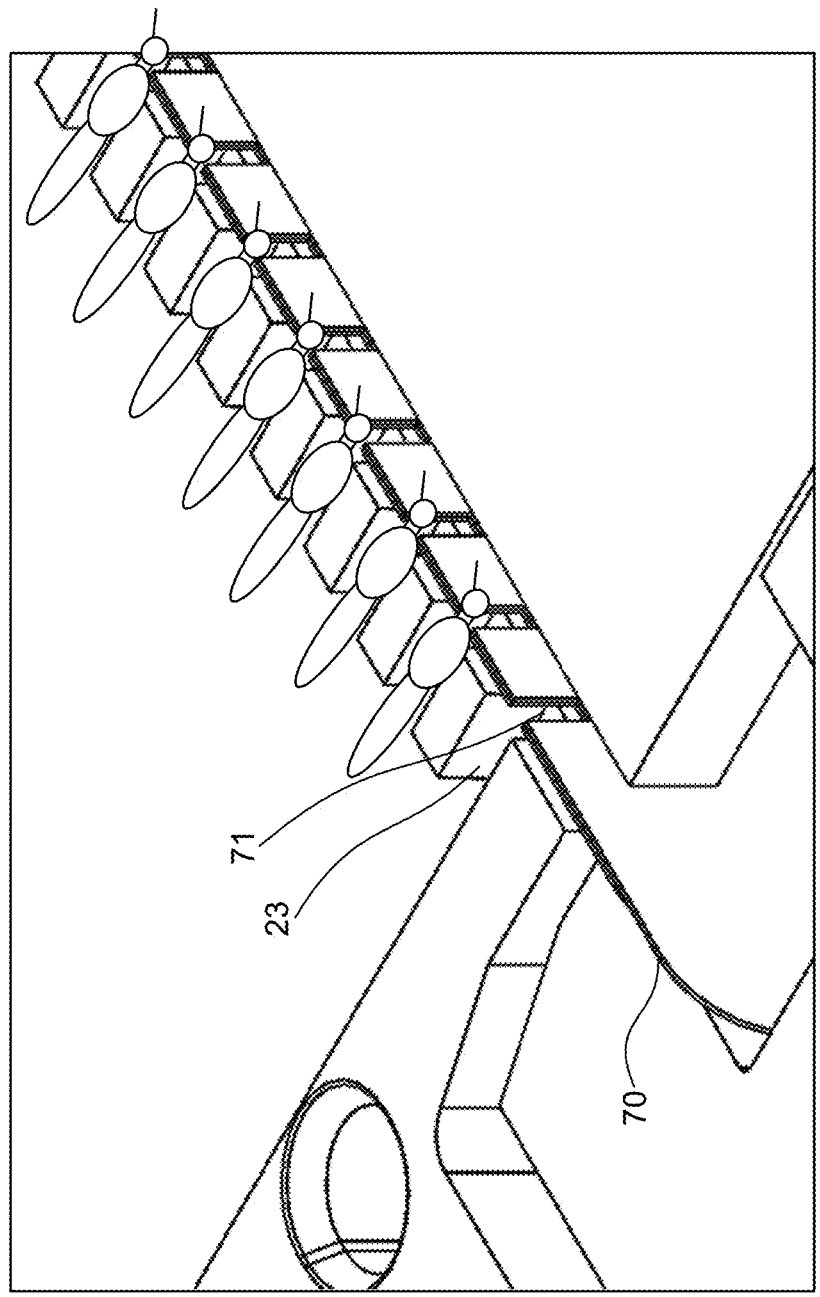
FIG. 16B is a detail of the cutting assembly and cartridge with the blades in the relaxed position and mosquitoes placed in slots.
Figure 16C:
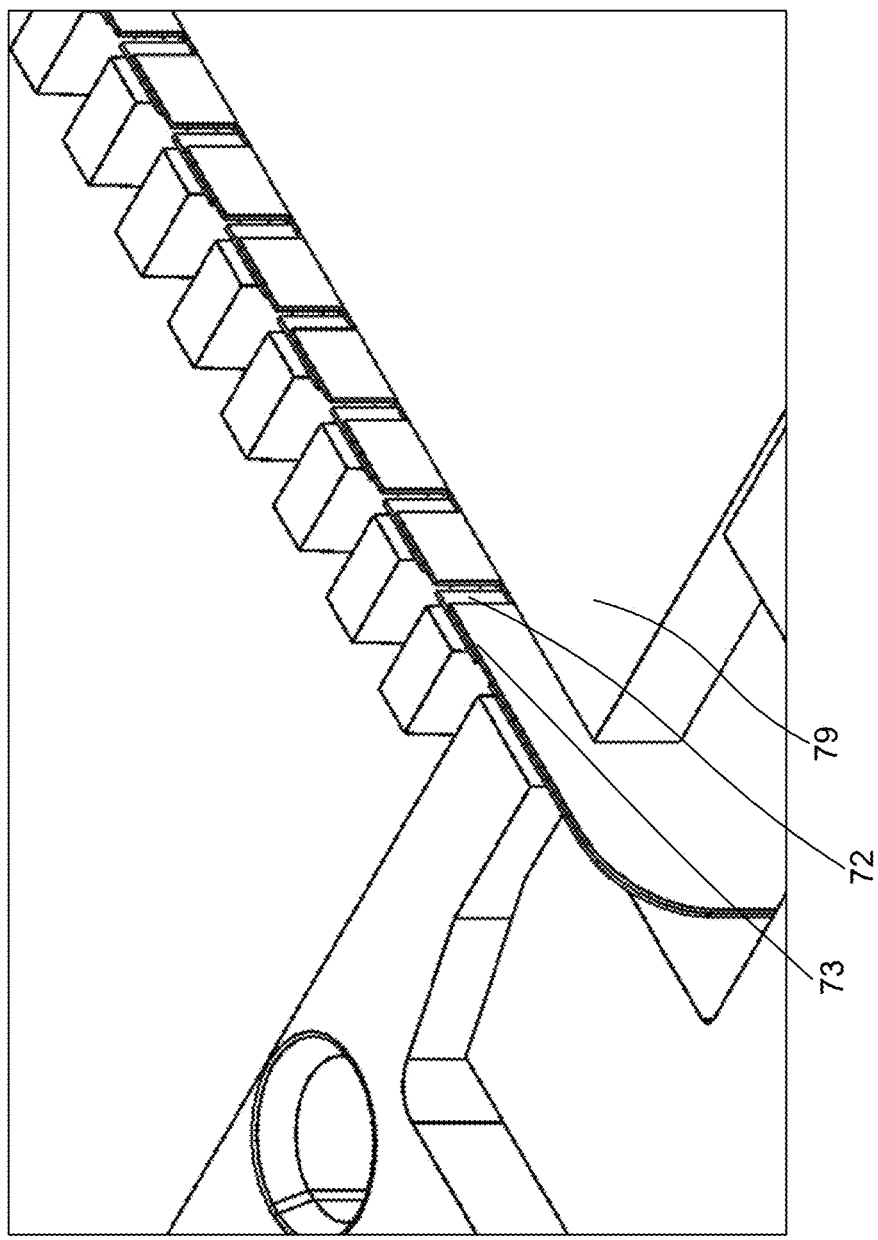
FIG. 16C is a detail of the cutting assembly, cartridge and slide with decapitated mosquitoes and heads on the slide.

FIGS. 6A-6B show an embodiment of a cutting (e.g., decapitation) assembly 40. The assembly has a thin channel 41 for the blade and is configured so that when the cartridge is docked with the assembly the channel is aligned with the edge of the cartridge. In this embodiment, a chamfer is provided to facilitate docking of the cartridge with the assembly. Other options will be apparent to one of ordinary skill in the art to accomplish the purpose of docking the cartridge with the cutting assembly so that a blade will decapitate all mosquitoes in the cartridge simultaneously, or in a coordinated progressively shearing fashion as would occur with a single bladed guillotine. The cartridge may be inserted into the apparatus either manually or automatically. The heads of all mosquitoes in the cartridge may then be cut off simultaneously by a cutting assembly 40 comprising a thin blade or by other means aligned within thin channel 41 in the cutting assembly (FIGS. 6A-6B). The blade itself may be actuated manually, by an automated device, or by a semi-automatic device such as a push-button actuated solenoid or motor. An opening in the cutting assembly permits all the heads to fall into a discard area 42. In an embodiment, the discard area further comprises a platform e.g., a disposable slide 79, facilitating the discard of the decapitated heads (FIGS. 15 and 16C). In an embodiment, a lavage means is provided to wash away debris and to clean the edge of the cartridge. In an alternative embodiment, a suction or wiping device is used to clear debris.

The width and depth of the slot is related to the average size of the subject mosquitoes. For example, for a population of mosquitoes with head width=0.56-0.65 mm, body width=1.35-1.55 mm, neck width=0.12-0.27 mm, the following dimensions of the slots may be chosen: slot width=1.75 mm, slot constriction at edge=0.8 mm, width of opening into staging area=2.7 mm. However, these dimensions are not critical so long as the bodies are reasonably constrained, the heads can pass through the edge opening and the bodies cannot pass through the opening, thereby leaving the neck protruding immediately adjacent to the front edge of the cartridge. The length of the slots is also not critical so long as the thoraces of the mosquitoes are aligned when the mosquito heads protrude beyond the edge. One advantage of this approach is that the legs and wings of the mosquito will tend to be dragged down the sides of the mosquito and out of the way.

Figure 8A:
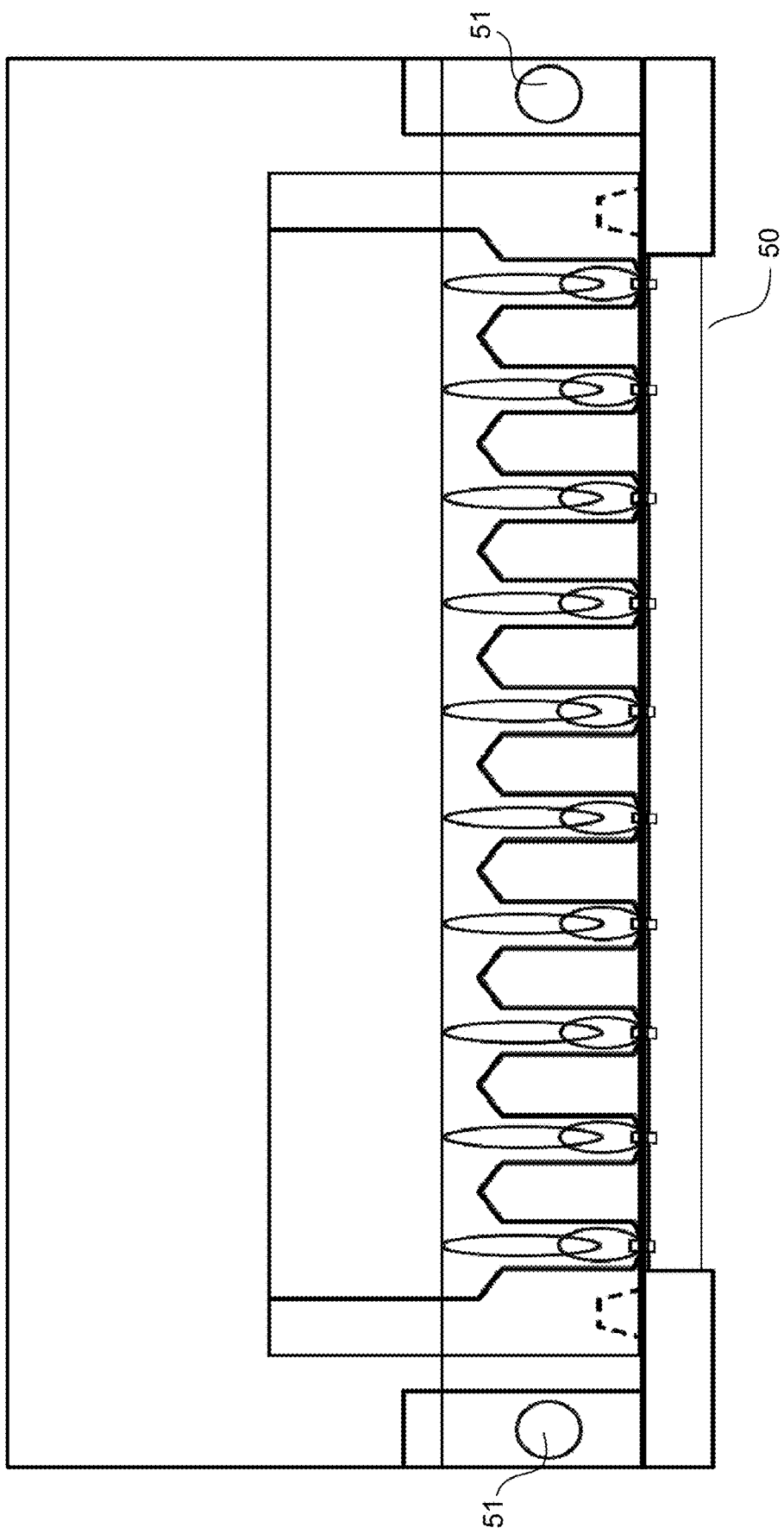
FIGS. 8A-8B depict a cartridge within a body squeezing assembly as well as a salivary gland receptacle.
Figure 8B:
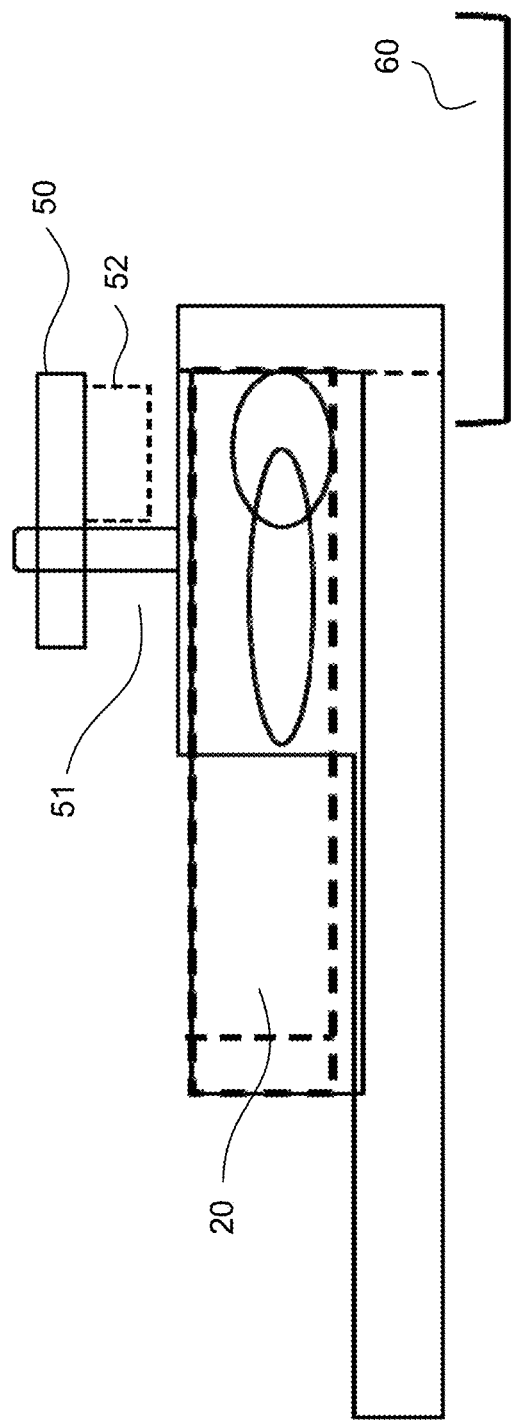

FIGS. 8A-8B show an embodiment of a body squeezer 50. In FIG. 8B, for example, the headless bodies in the cartridge are squeezed simultaneously with multiple "fingers" 52 that extend from the squeezer block 50 and can operably pushed down through the slots. In this embodiment, two guide pins 51 guide a squeeze plate in order to engage squeezing fingers simultaneously on the thoraces of all mosquito bodies in the cartridge. In an embodiment, mechanical stops limit the downward travel of the squeeze plate. In some embodiments, stops are not included, and instead the lengths of the fingers are configured to apply appropriate pressure when squeezed. The depths of the slots is not particularly critical if each finger aligns and fits within the slot and the fingers are configured to reach the mosquito thoraces. The finger 52 lengths are chosen so that the salivary glands are extruded from the thoraces when pressure places the squeezer 50 in its full downward position. In an embodiment, lavage is used to convey the salivary glands into a collecting basin or channel, from which they are transferred to a suitable storage container for future processing. In this embodiment, alignment pins and stops are used to align the cartridge with the assembly. However, other options will occur to one of ordinary skill in the art to accomplish the purpose of docking the cartridge with the squeezing assembly so that the squeeze plate will engage all the thoraces simultaneously (It should be noted that a similar arrangement may be used in one alternative embodiment for the head-cutting assembly illustrated in FIGS. 6A-6B.). The cartridge may be inserted into the apparatus either manually or automatically, and the squeezing action may be actuated manually, by an automated device, or by a semi-automatic device such as a push-button actuated solenoid or motor. A force sensor or slip clutch assembly may be incorporated to limit the force exerted by the squeeze plate onto the thoraces.

Figure 9A:
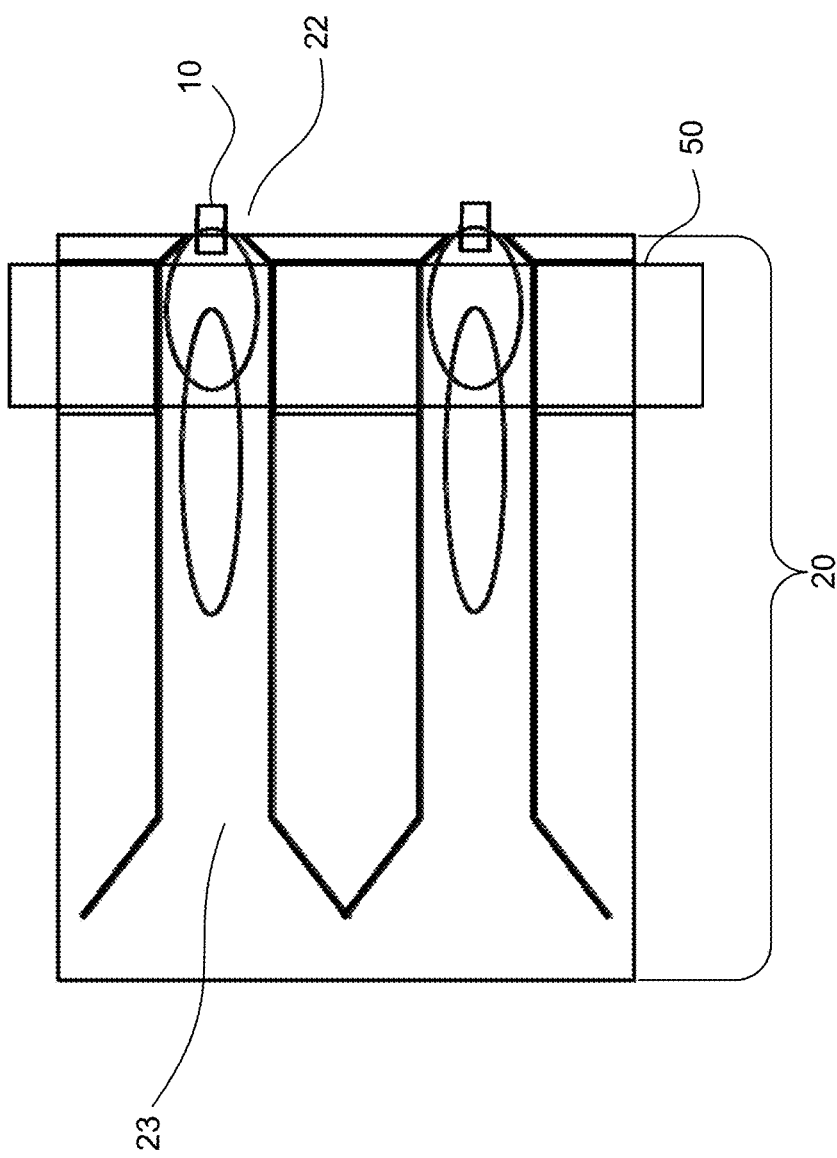
FIGS. 9A-9B show details of a cartridge within an embodiment of a body squeezing assembly.
Figure 9B:
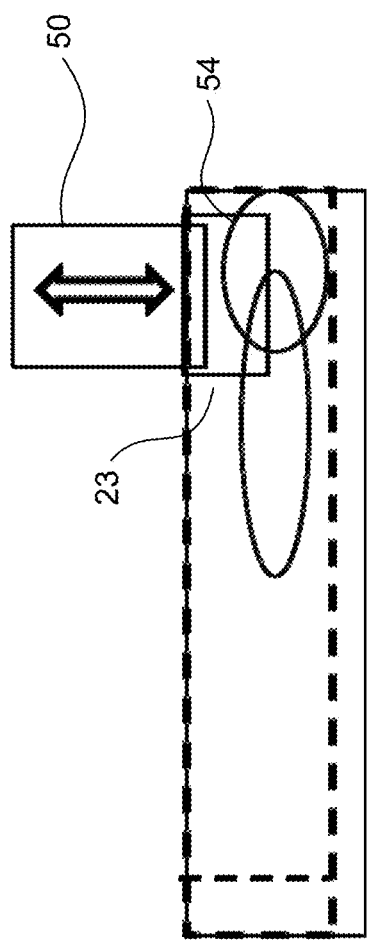
Figure 10A:
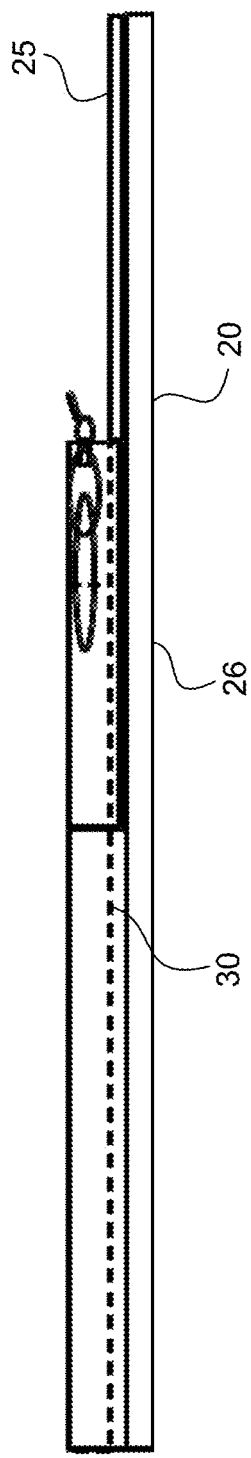
FIGS. 10A-10B depict a work station device incorporating several assemblies, including a staging area, a cutting assembly, and a body squeezing assembly.
Figure 10B:
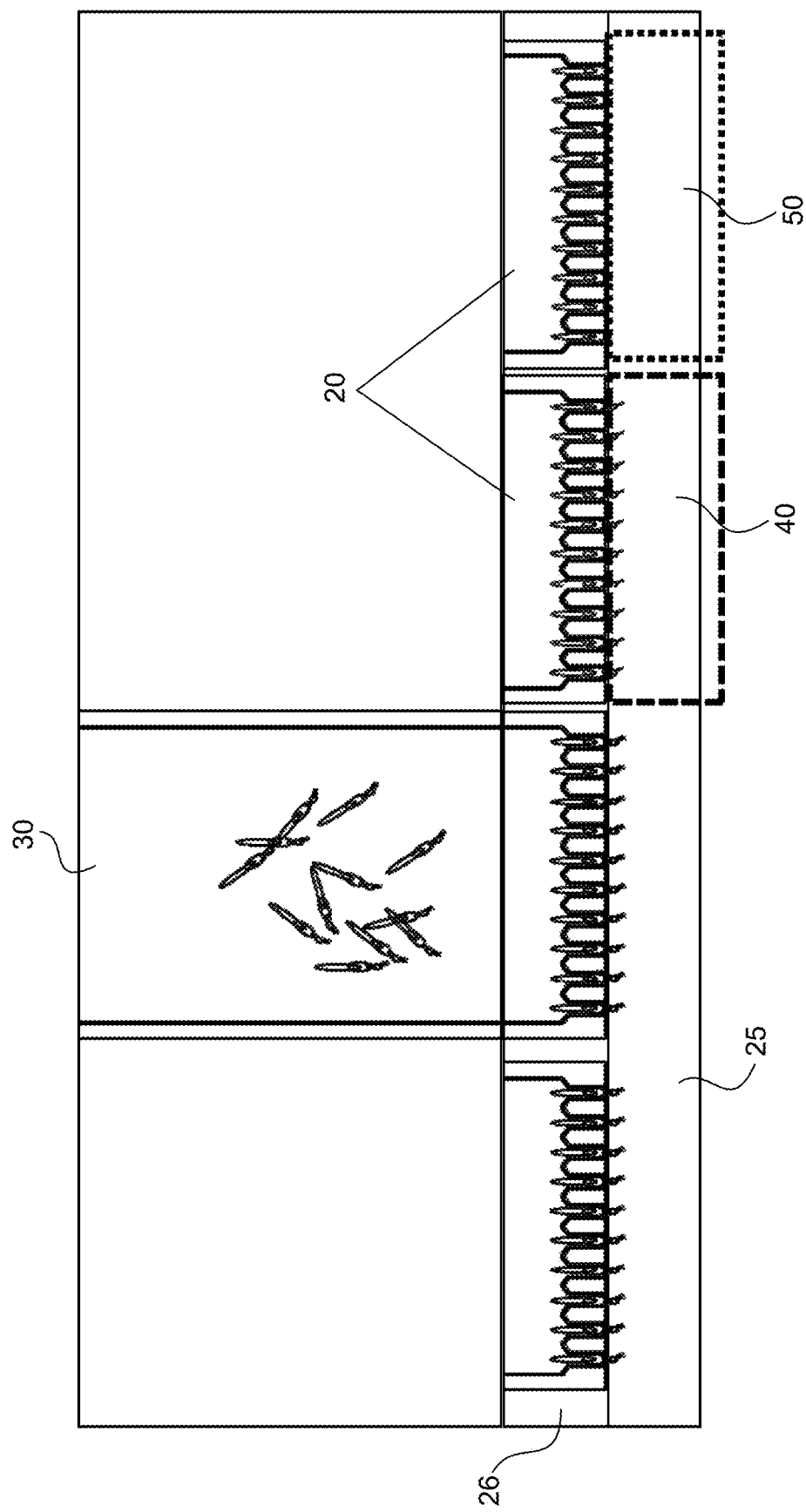

FIGS. 9A-9B show yet another embodiment of a body squeezer. In this embodiment, rather than fingers reaching into each mosquito slot, a lateral groove 54 is cut across the cartridge, allowing a simple rod, bar, or block to compress all the thoraces simultaneously. In this embodiment the groove is shallow relative to the mean mosquito body thickness so that a mosquito body squeezer comprising the rod, bar, or block can operably press down simultaneously on all of the thoraces. The advantage of this design choice is that the lateral alignment of the cartridge relative to the squeezing assembly is less critical than a design in which squeezing fingers are extended into each mosquito slot. Thus, the alignment pins may be eliminated, especially if a workstation arrangement similar to that in FIGS. 10A-10B is adopted. The depth of the slots is chosen so that the thoraces are compressed an appropriate amount to extrude the salivary glands but to limit the extrusion of extraneous material. In both the embodiments of FIGS. 8A-8B and 9A-9B, the top surface of the cartridge may be used as a reference datum for controlling the depth of squeezing. Alternatively, force sensors or springs may be used to control the squeezing force. Or these may be used in combination.

Similarly, the front edge of the cartridge may be used to provide a locating means for aligning the cartridge (and, hence, the necks) relative to the blade of a cutting assembly for cutting off the heads. The sides of the cartridge may also be used to align the cartridge with the squeezing mechanism. Alternatively, fingers 52 can be configured as guide holes, pins, or other similar means known in the art that may be used to achieve the desired alignment.

Figure 7A:
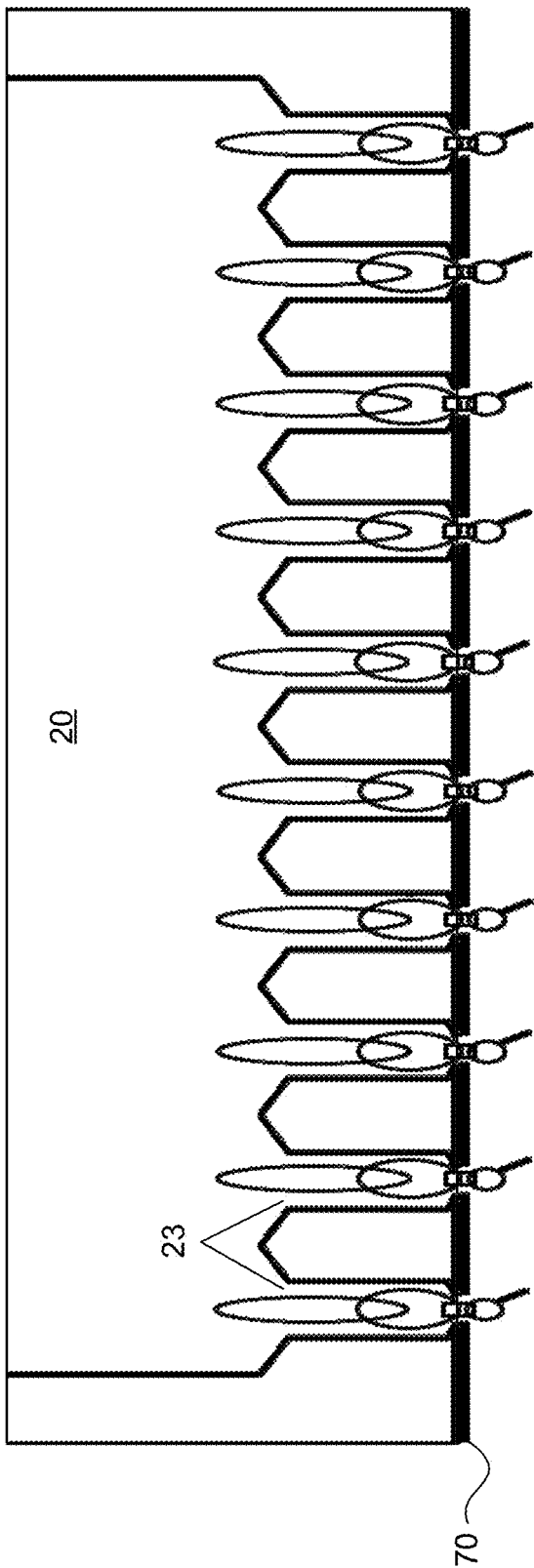
FIGS. 7A-7D depict a cutting assembly comprising a pair of notched blades.
Figure 7B:
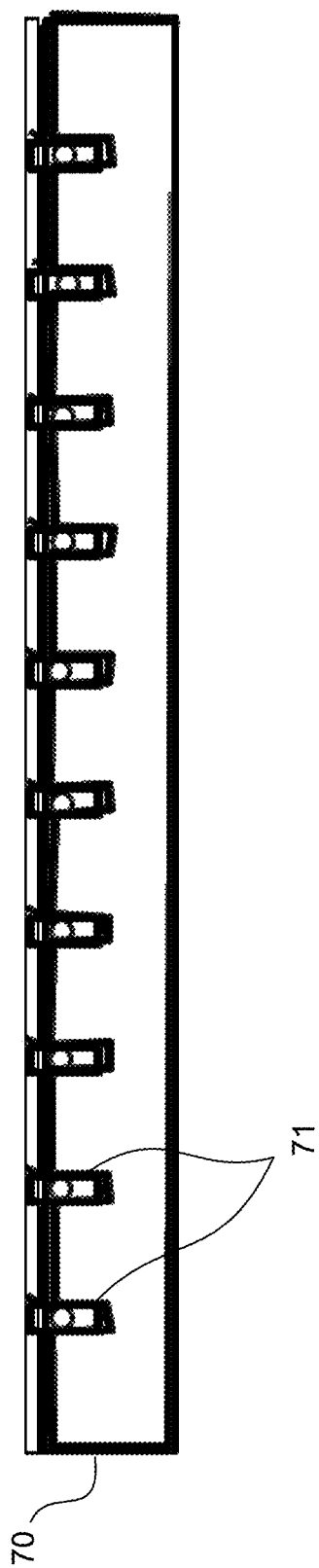
Figure 7C:
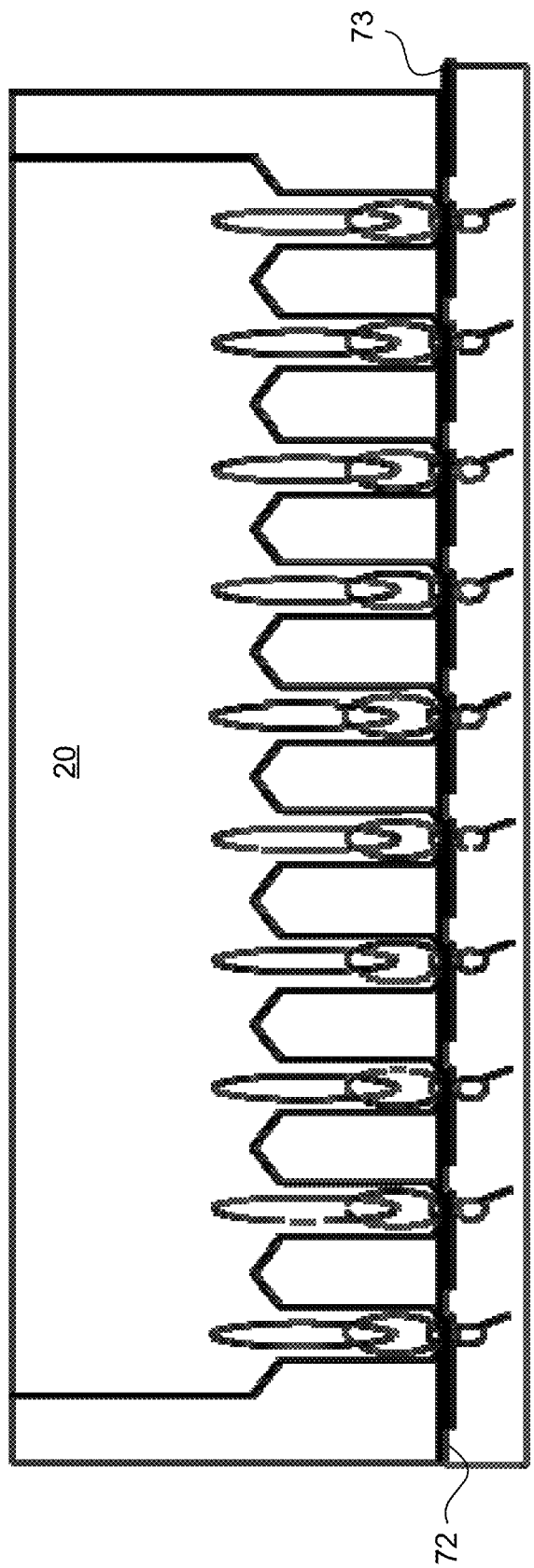
Figure 7D:
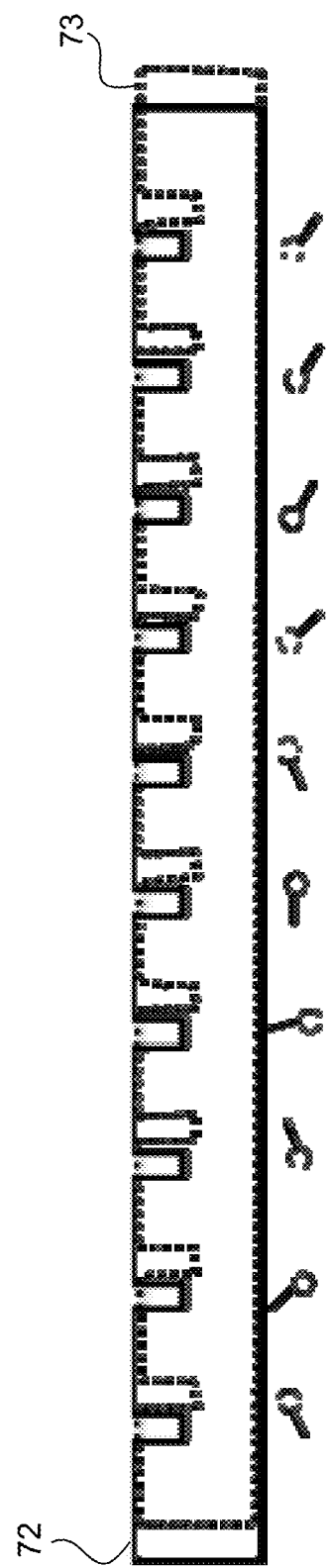

FIGS. 7A-7D show another embodiment of a mosquito cutting/decapitation assembly. As shown in FIG. 7B, a blade pair 70 (e.g., a serrate blade pair) is adjacent to the front edge of the cartridge. The notches 71 of each blade are initially aligned with each other and with the slots of the cartridge 23. The heads of all mosquitoes in the cartridge are passed through the paired notched blades (Blade 1 72 and Blade 2 73) so that the necks are positioned in the notches of the blades (FIGS. 7A-7C). In this embodiment, constraint of the bodies of the mosquitoes in the cartridge slots results from the dimensional width of the notches in the paired blades, which is wide enough to permit passage of mosquito necks and heads but too narrow to permit passage of mosquito bodies. Operationally one of the blades 72 may then be displaced sideways relative to the other blade 73 and to the cartridge, as depicted in FIGS. 7C and 7D, severing the necks and decapitating all mosquitoes in the cartridge thereby. The heads will then fall away and be collected in any convenient manner. The two blades are mechanically arranged and supported so that they remain in close proximity and parallel to each other. In an embodiment they are both attached to the cartridge. In another embodiment they are attached to a cutting assembly 40 against which the cartridge may be pressed. In yet another embodiment a first blade is affixed to the cartridge and a second blade is affixed to a structure against which the cartridge and first blade may be pressed. In other embodiments, the cartridge is constructed to have a narrowed opening through which the necks pass and a single notched blade may be used to cut off the heads. An advantage of embodiments using the two blade embodiments described is that the mosquito bodies are less likely to be displaced in their compartments during head removal, thus remaining better aligned for subsequent squeezing of the thoraces for salivary gland removal. One advantage of incorporating both blades into a cutting assembly structure against which the cartridge is removably affixed is that the openings in the cartridge do not need to be narrowed to help align the necks. This simplifies both construction of the cartridges as well as the process of squeezing the salivary glands into a receptacle at a squeezing station after the heads are removed. Another advantage is the removable cutting assembly is more easily cleaned. In the case where both blades are attached to a cutting assembly structure, either or both blades may be displaced laterally to sever the necks.

FIGS. 10A-10B show an embodiment of a workstation arrangement for executing the workflow of the method of use. In this case the cartridges 20 are placed into a track 26 that holds them in the desired alignment relative to the staging area 30, cutting assembly 40, and body squeezer (salivary gland extraction) 50 sequentially. Suitable stops or detents can be used to provide the needed lateral alignment with the head removal and thorax squeezing sub-stations. However, it will be readily apparent to one of ordinary skill that many alternative arrangements may be used.

Figure 11:
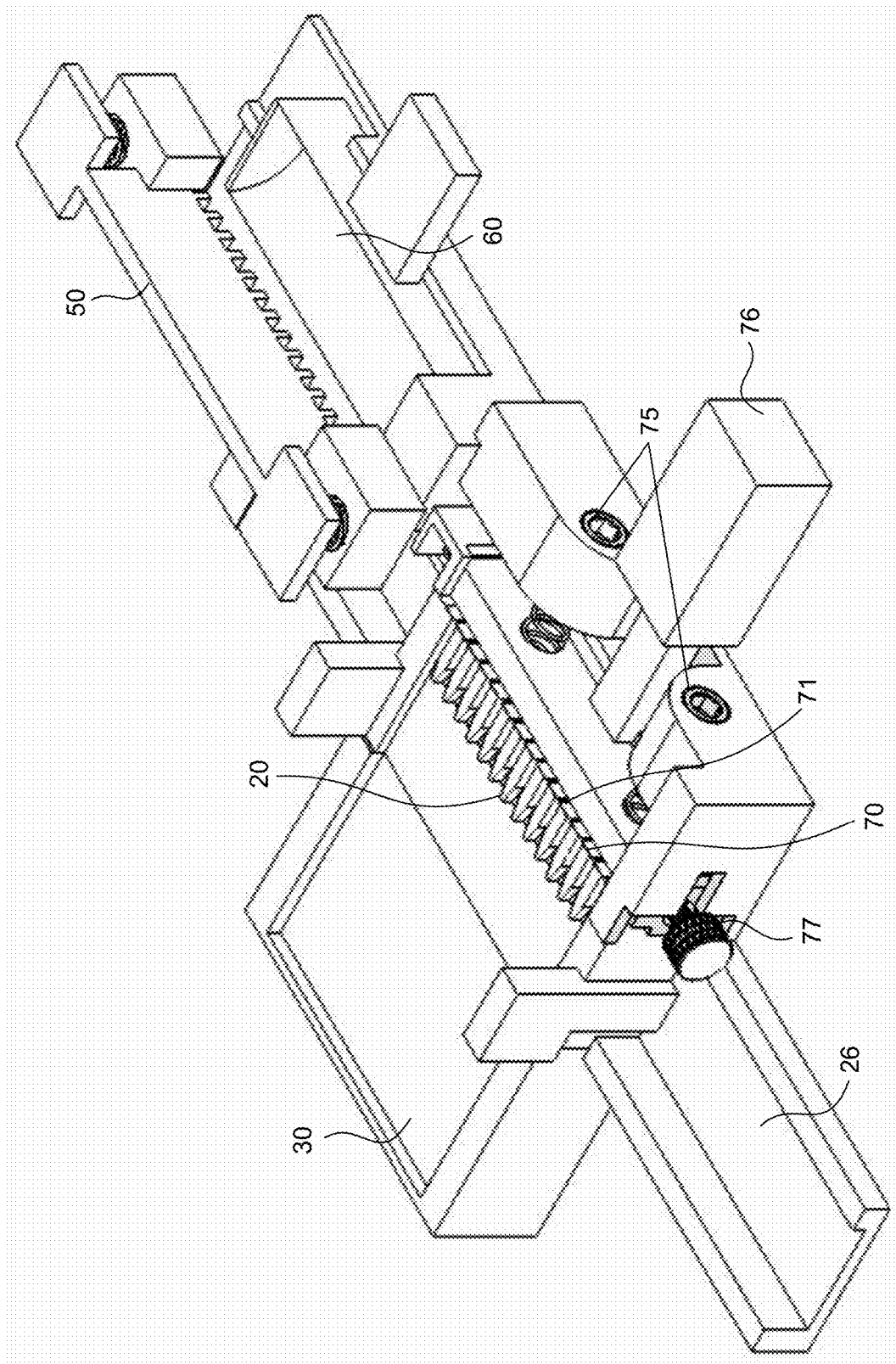
FIG. 11 depicts an integrated device incorporating several assemblies, including a staging area, a cutting assembly, and a body squeezing assembly and a cartridge track for moving cartridges from one operational area to the next.
Figure 12:
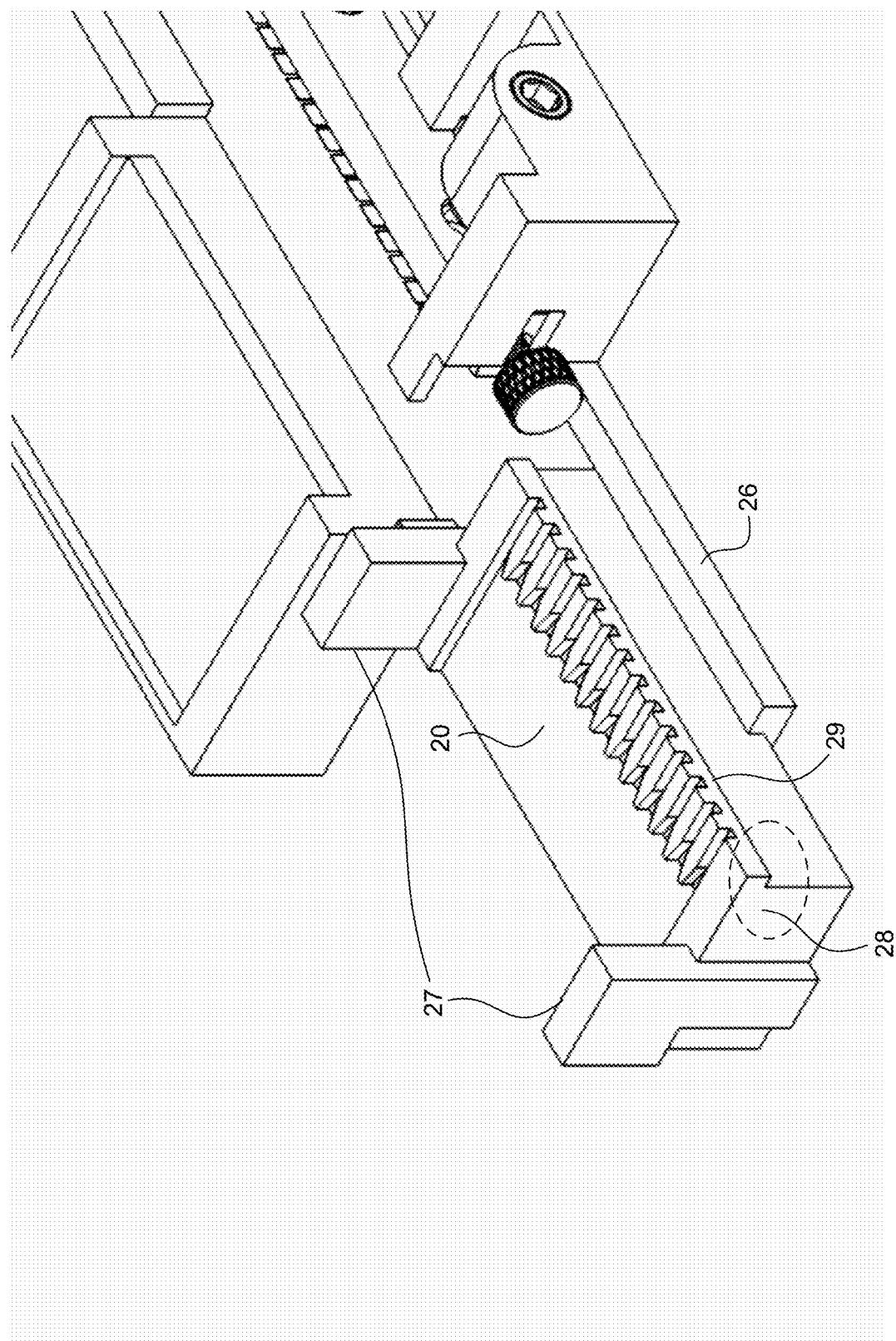
FIG. 12 depicts a detail of a cartridge in a cartridge track.

FIG. 11 shows an embodiment of a combined apparatus for salivary gland extraction comprising a mosquito staging area 30, a guide track 26 for slotted cartridges, a slotted cartridge 20, a cutting assembly 40 and blade pair 70, a mosquito body squeezer 50 and a receptacle 60, serving as a salivary gland collection tray. Removable cartridges 20 are placed in a guide track 26 that assists in positioning them at different positions along the track. FIG. 12 shows a cartridge that has been loaded into the apparatus. FIG. 11 shows a cartridge in position for loading mosquitoes into the cartridge slots and blade notches 71 for decapitation. A mosquito staging area 30 is used to contain mosquitoes to be loaded into the cartridge. In this position, blade pair 70 is pressed by springs 75 against the cartridge, also holding the cartridge firmly against the mosquito staging area 30. In this embodiment, the "fixed" blade is the one closest to the cartridge and the "moving" blade is the one between the fixed blade and the rest of the cutting assembly. Suitable stops or detents hold the cartridge in position along the track so that the centers of the cartridge slots line up with the notches in the cutting assembly blades when the blades are in the open position. A handle 76 is used to relieve the pressure of the springs on the cartridge, permitting it to be slid along track 26 when changing positions of the cartridge along the track. A push button 77 is used to push one of the blades from the open to the closed (cutting) position. A small spring (not shown) pushes the blade back into the open position when the button is released. In other embodiments, actuation may be done automatically, by pulling on a lever, or any other convenient means.

This embodiment also comprises a squeezer 50 and salivary gland collecting receptacle 60. In some embodiments the cartridge 20 comprises handles 27, depicted in FIG. 12 that may be used to help guide the cartridge along track 26. The cartridge may also comprise a small ledge 28 that is so constructed that the ends of the cartridge slots 21 containing the mosquito bodies overlap the collecting receptacle 60 (FIG. 11) when the cartridge is in position for thorax squeezing by means of the body squeezing assembly, to extract the salivary glands.

Figure 13A:
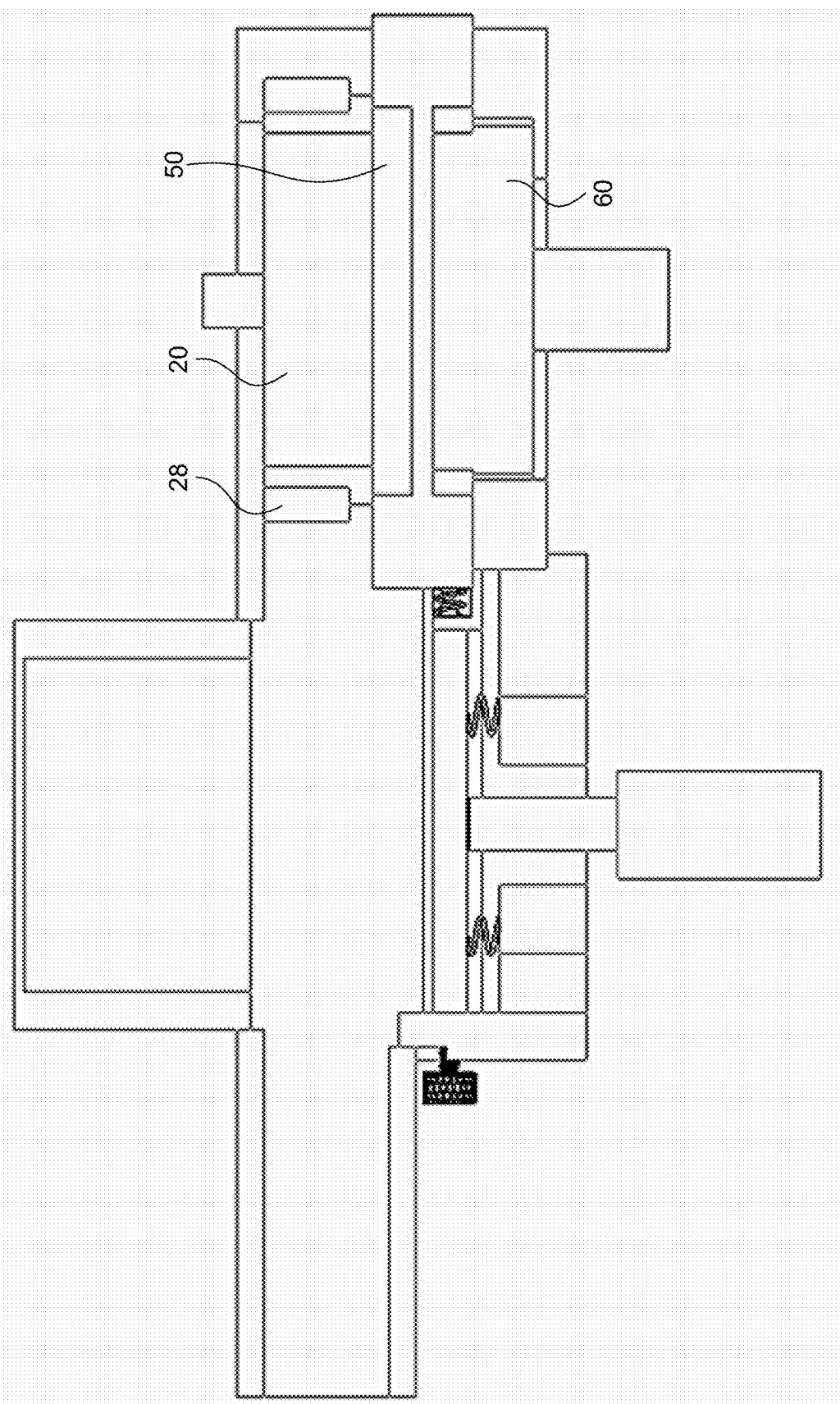
FIGS. 13A-13B show details of an integrated device showing the body squeezing assembly.
Figure 13B:
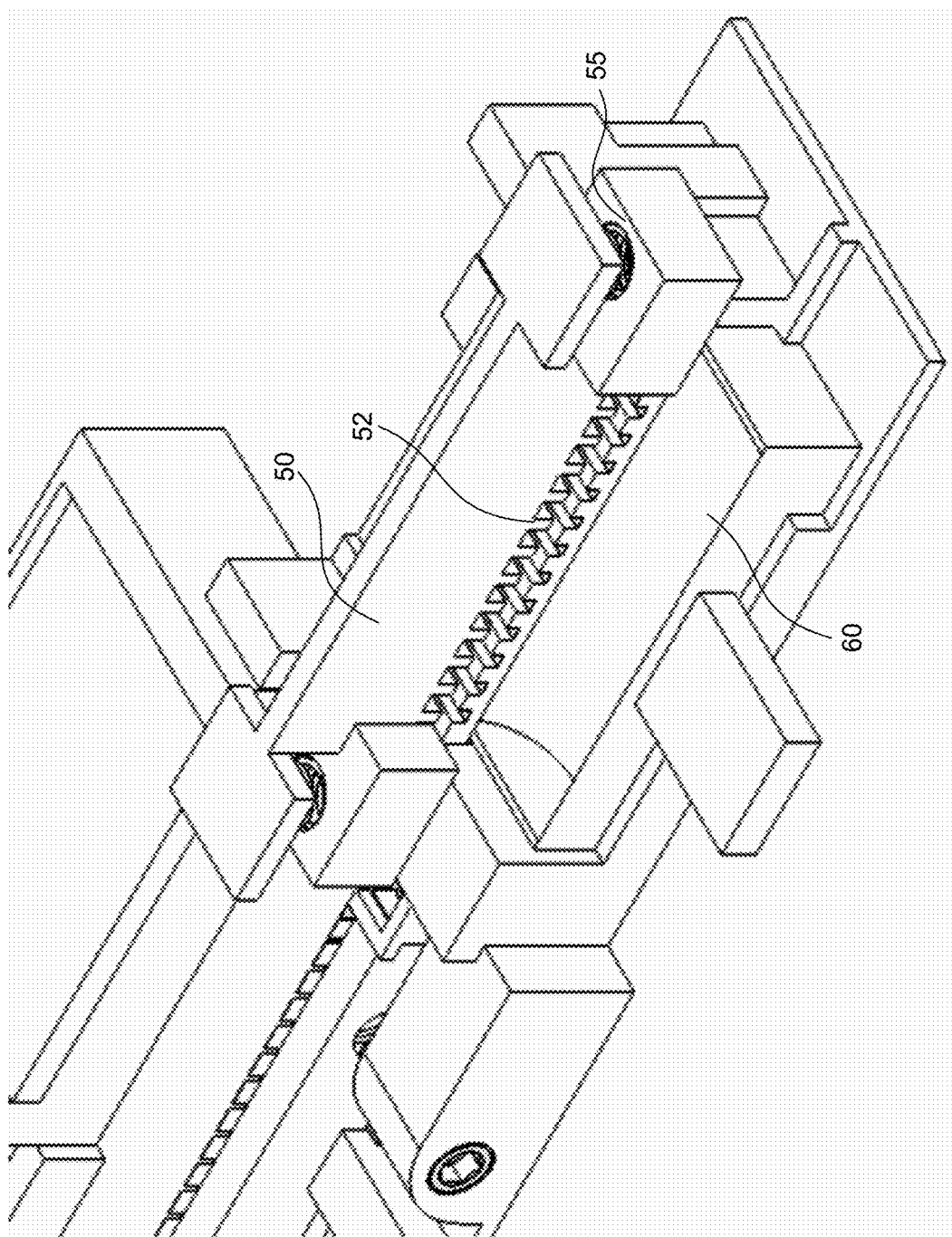

FIG. 13A shows a top view of the body squeezing assembly of the device when the cartridge 20 is in position for squeezing the thoraces 11 of the mosquitoes to extract the salivary glands. FIG. 13B shows an oblique view when the cartridge is in the same position. Note that the ledge 28 on the cartridge causes the front edge of the cartridge to overhang the receptacle 60. The body squeezer 50 comprises a vertical plate with serrate notches and fingers such that the fingers 52 are constructed to align with and fit within the cartridge slots 23 with sufficient clearance so that the fingers can extend into the slots when the cartridge is positioned to receive the squeezing assembly. A suitable detent or spring loaded latch mechanism is used to help secure the cartridge in the correct alignment along the track so that the fingers 52 line up with the cartridge slots 23. In this embodiment, the body squeezing assembly is actuated by pressing down on it manually against springs 55, which then return it to the retracted position when pressure is removed. In other embodiments, actuation may be done automatically, by pulling on a lever, or any other convenient means. Similarly, in another embodiment, the squeeze plate simply be picked up and manually aligned with the cartridge slots 23 to squeeze the thoraces. Or a different squeezing design may be used in which a bar is placed into a slot fabricated (See FIG. 8A-8B) in the cartridge perpendicular to the mosquito-holding slots 23 in a position corresponding to the thoraces.

After the salivary glands have been extruded using the squeezer 50, in an embodiment, they are extracted from the mosquito and collected by vacuum, by washing or by wiping into the receptacle 60. In another embodiment, the salivary glands are gathered by suction. It may be advantageous to hold the squeezing assembly in the squeeze position while this is done. In an embodiment, this is accomplished by maintaining pressure against the springs 55. In yet another embodiment, a latch/release mechanism (not shown) is be used to hold the squeezing assembly in the squeeze position while the salivary glands are gathered or transferred to the receptacle 60. The latching mechanism is then released once the salivary glands are transferred or gathered. The squeezer 50 and latch/release mechanism may be actuated, either manually, automatically, or semi-automatically.

The cartridges and other components and assemblies of the device may be made of any suitable material, although materials including but not limited to stainless steel, which are easily cleaned and sterilized and are compatible with manufacturing of biological products in compliance with cGMPs are preferred. A sample workflow for using this apparatus is presented below. It will be readily obvious to one of ordinary skill that many refinements or modifications to this apparatus and method are possible without changing the fundamental nature of what is proposed.

In an embodiment of use, mosquitoes are placed in the staging area 30. They are grasped one at a time and slid into the individual slots 23 of the cartridge 20 so that their heads 12 protrude beyond the end of the cartridge. One technique for doing this is to grasp the proboscis 14 of a mosquito and use it to drag the mosquito along the slot until its head 12 protrudes and its body comprising the thorax 11 are stopped by the constriction at the end of the slot or the constriction of the cutting blade. One advantage of this method is that the head 12 and neck 13 will be conveniently aligned for decapitation. Once the mosquitoes are positioned in parallel in slots within the cartridge, a cutting assembly 40 comprising a blade is operationally applied such that the blade simultaneously passes through the necks of all mosquitoes in the cartridge, decapitating the mosquitoes thereby. Subsequently, a mosquito body squeezer 50 is operationally applied such that the thoraces of all mosquito bodies in the cartridge are pressed, extruding the salivary glands into a salivary gland collection trough 60.

In the foregoing, the present invention has been described with reference to suitable embodiments, but these embodiments are only for purposes of understanding the invention and are not intended to limit the claims that follow. Various alterations or modifications are possible so long as the present invention does not deviate from the claims.

Example Workflow

Step 0. Place a quantity of mosquitoes onto the staging area 30. Typically, there will be a larger number of mosquitoes than slots in any individual cartridge. Typically an aqueous liquid or other medium may also be included with the mosquitoes and can help provide lubrication while the mosquitoes are being placed into the slots of the cartridges. The supply of mosquitoes in the staging area may be replenished at any time.

Step 1. Place a cartridge 20 into the apparatus track 26. Use the handle 27 on the cartridge to move the cartridge proximate to the cutting assembly 40. Compress the springs sufficiently to permit the cartridge to slide along the track to the correct position relative to the cutting assembly and release the handle to engage the detent or stops to hold the cartridge in the correct position for head removal. Alternatively, the handle can be released once the cartridge is far enough into the track so that it will slide smoothly along the track until it reaches the correct position for head removal.

Step 2. Transfer mosquitoes into the cartridge slots 23. For each mosquito, grasp the mosquito by its proboscis 14 and place it into the slot so that its neck is engaged in a notch 71 within the cutting blades 70. In doing this, it is helpful to lift the mosquito slightly when the head gets close to the blades and then lower it so that the neck is in the proper position.

Step 3. Cut all the heads off by pressing on the cutting assembly button 77 and releasing it.

Step 4. Disengage the cartridge from the cutting assembly by pulling back on the handle 27 and slide the cartridge along the track until it is properly positioned relative to the thorax squeezer 50.

Step 5. Press down on the thorax squeezer to extrude the salivary glands out of the thoraces.

The salivary glands will be extracted from the mosquitoes and collected in the collecting receptacle 60. If necessary, one may use lavage from a squeeze bottle or other source to wash any glands that have remained stuck to the cartridge into the receptacle. If the receptacle is full, empty it into a collecting container. Alternatively, one can modify the apparatus so that the salivary glands and fluid may be suctioned into a collecting container or collecting system, or the collecting receptacle can be modified so that the glands and fluid flow continuously into a collecting system.

Step 6. Optionally, brush or wash the heads from the cutting assembly.

Step 7. Optionally, repeat steps 1-6 as often as necessary.

Additional Embodiments

Figure 14:
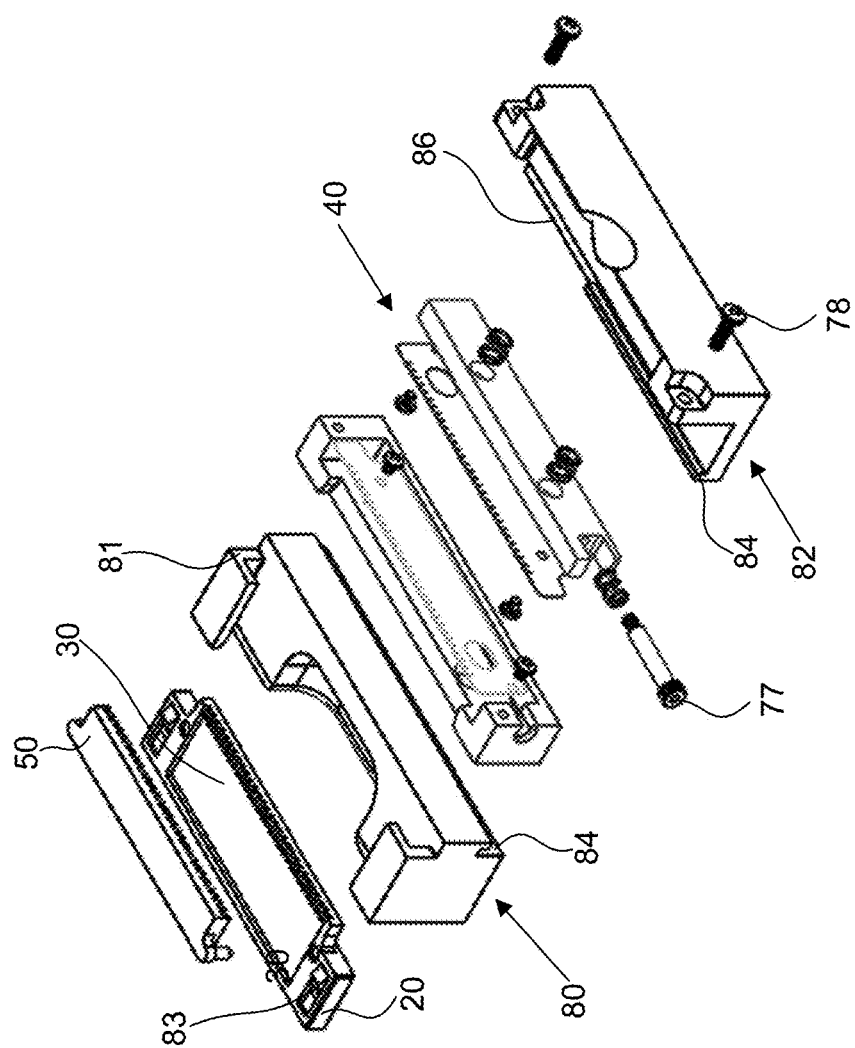
FIG. 14 is an exploded view of the relationship among the rear base, front base, cutting assembly, slotted cartridge, and slide.

Characteristics of each of the alternative embodiments described herein may also apply to each of the other alternative embodiments. In alternative embodiments functional elements of the salivary gland extract device are provide as separate elements as shown in FIGS. 14 (exploded view) and 15 (assembled), for example. The rear base 80 is adapted to align with the front base 82, for example with respect to rear edge 86 of front base 82. In an embodiment, this alignment is facilitated by a tongue and groove 84. As depicted, the tongue is integrated proximate to the bottom rear of the front base 82 and the groove is integrated proximate to the bottom front of the rear base 80, however, in an embodiment the rail is on rear base 80 and groove is on the front base 82. The tongue and groove are configured such that, when assembled the front and rear bases are aligned in the desired functional relationship.

The cutting assembly 40 (shown in isolation in FIG. 16A) may be a unit that is separable from the cartridge and slots, but in use may be affixed to the front base 82 and oriented toward the rear base 80, as shown in FIG. 15. As shown in FIG. 15, the cutting assembly is affixed to the front base by a pair of screws 85, but other means for attachment are known to those skilled in the art. In an embodiment, the assembled cutting assembly 40 and front base 82 is configured to receive a disposable slide 79 located below the slots 23 of the cartridge and notches 71 of the cutting assembly and configured to receive the heads of decapitated mosquitoes.

The rear base 80 is adapted to receive the slotted loading cartridge 20 in which the mosquito staging area 30 and slots 23 are disposed. To facilitate the alignment of the loading cartridge with the other functional elements of the device, shoulders 81 are provided on each side of the rear base 80. In this regard, the shoulders serve to align and guide the cartridge toward the front of the rear base. As shown, the slots 23 of the cartridge may be relatively short, similar to those shown in FIG. 5; in FIG. 5 the staging area and slots are separable. In these embodiments the preferred number of slots is between about 5 and 100, 10 and 50, and 20 and 40. For example, FIG. 14 depicts a loading cartridge with 30 slots. Turning to FIG. 16B, the cutting assembly 40 may blade pair 70 adjacent to each other (also shown in FIGS. 7A-7D). One blade 73 is closest to the front base and the other blade 72 is closest to the rear base. Each blade comprises a series of notches 71 configured to correspond to the slots 23 of the cartridge. In a first mode, e.g., a default, relaxed mode, the slots of the two blades are aligned with each other and adapted to receive the heads and necks of each of the mosquitoes placed in the cartridge slots. In a second mode, e.g., an operational mode when the cartridge is operationally aligned with the cutting assembly 40, the slots 23 of the cartridge abut and align with the notches 71 of the cutting assembly.

Suitable stops or detents 83 can be used to provide the needed lateral alignment with the rear base, the aligned front and rear bases, and the cutting assembly. However, it will be readily apparent to one of ordinary skill that many alternative arrangements may be used.

As shown in the figures, when the front base 82 and cutting assembly 40 are assembled they configure to receive a removable slide 79, such that an edge of the slide is adjacent to the blade pair 70 and the slide surface is below the notches.

As shown in FIG. 15, when operationally assembled, the rear base 80 is removably affixed to and aligned with the front base 82. As shown, the cutting assembly 40 comprising the blade pair 70 is removably affixed to the front base such that the blade pair 70 faces the rear base 80. Then, cartridge 20 slides into the rear base such that the leading edge abuts the cutting assembly and each slot 23 of the cartridge aligns with a corresponding notch in the blade pair. In some embodiments, a mosquito is placed within each slot 23 such that its neck rests in a notch of the blade pair 70 and its head is above the slide 79. Common features of the cutting assembly are much the same as shown in FIG. 11, for example.

To remove the mosquito heads, the blade pair is activated by pushing the button 77 to move the blades laterally relative to each other from an open position to a closed position, as shown in FIG. 16C, for example. In some embodiments, button 77 may be spring loaded, for example, such that it is biased in an open configuration. For ease of disposal, the decapitated mosquito heads are collected on the removable and disposable slide 79.

Figure 17A:
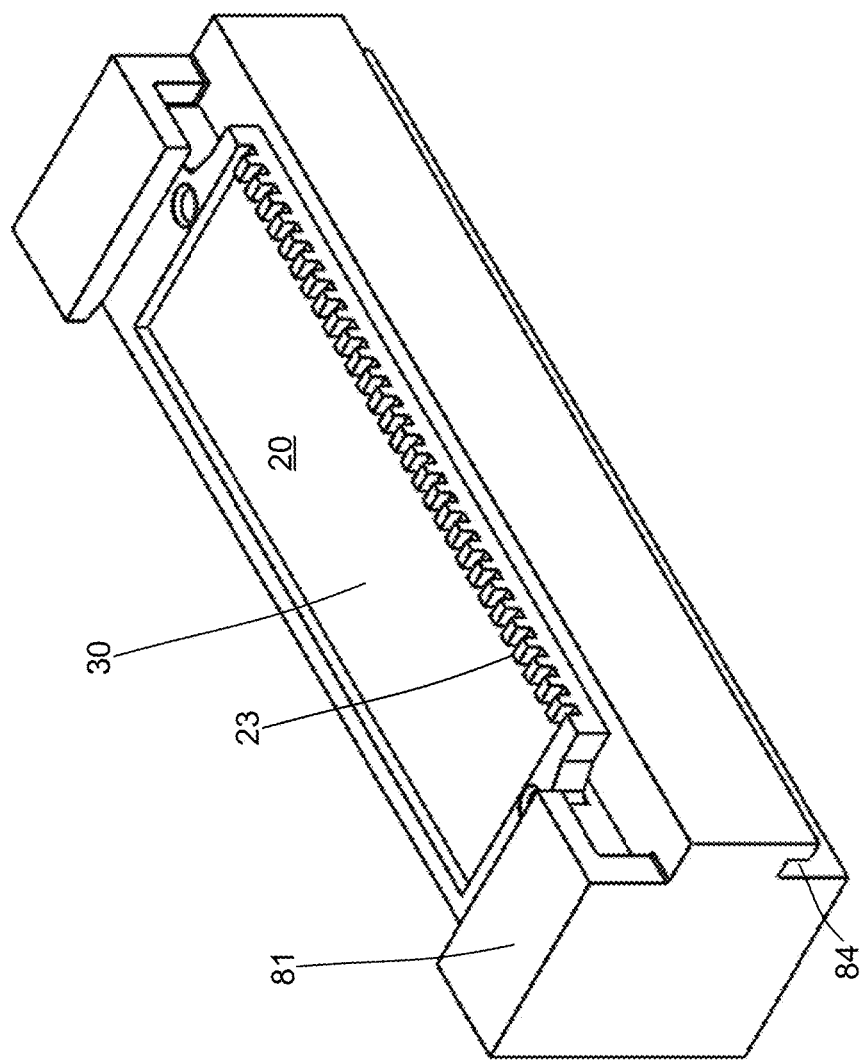
FIG. 17A shows the rear base and cartridge.
Figure 17B:
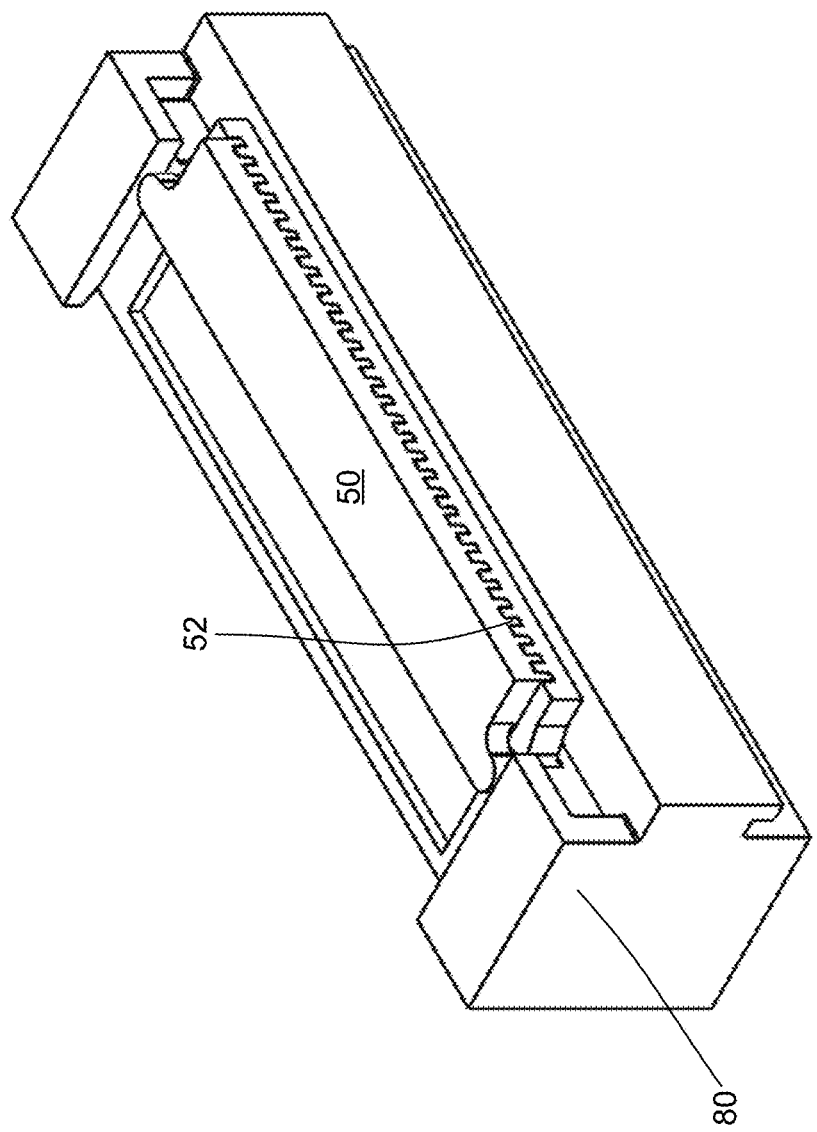
FIG. 17B shows rear base and cartridge with the squeezer fingers placed in the slots.

As shown in FIG. 17B, a squeezer 50 is configured with fingers 52, each finger configured to fit within a slot of the cartridge. In some embodiments, the length of the fingers are such that when the squeezer 50 is coupled to the cartridge and pushed down, the fingers apply sufficient pressure to extrude the mosquito salivary glands from the mosquito. In some embodiments, each finger fits within a separate, corresponding slot of the cartridge.

Turning to FIG. 16C, after decapitation of the mosquitoes, the rear base and cartridge with decapitated mosquito bodies may optionally be separated from the front base for ease of subsequent operations.

Figure 17C:
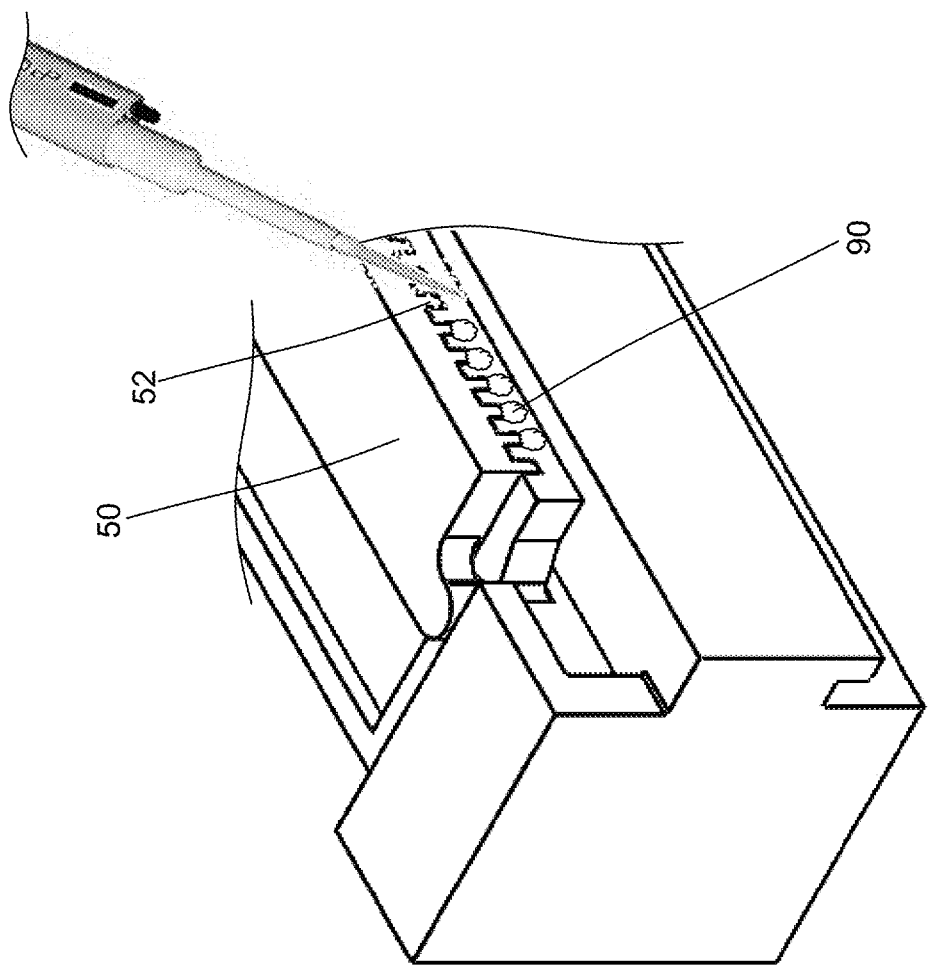
FIG. 17C is a detail showing the extruded salivary glands and a means for collecting them.

As shown in FIG. 17A, the base and cartridge with decapitated mosquitoes in their slots may be placed on a level service. As illustrated in FIG. 17C, the squeezer 50 is placed onto the cartridge and such that the fingers 52 are within the slots 23 of the cartridge 20, pressure is applied to the squeezer and the salivary glands 90 are extruded thereby.

Once extruded from the mosquito bodies, salivary glands may be extracted, collected and pooled, for example by a vacuum tool or suction tube (shown in FIG. 17C for example) or similar means known to those skilled in the art.

In an embodiment, the cartridge, slide, and squeezer are intended to be used once for each round of salivary gland extraction, removed and discarded, while the front and rear bases and cutting assembly may be intended for multiple rounds of use. In some embodiments, the entire assembly including the front and rear bases and cutting assembly may be intended for multiple rounds of use.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

REFERENCES

[1] -----, "Mosquito-Borne Disease," http://en.wikipedia.org/wiki/Mosquito-borne_disease, 2015.

[2] A. E. Brown and F. Catteruccia, "Toward silencing the burden of malaria: progress and prospects for RNAi-based Approaches", *BioTechniques* (2006) 40(S4):S38-S44.

[3] -----, "Malaria," http://www.cdc.gov/malaria/.2015.

[4] I. Lapowsky, "The Next Big Thing You Missed: This Mosquito-Dissecting, Malaria-Killing Robot Needs Your Help", *Wired,* 2014, http://www.wired.com/2014/06/the-next-big-thing-you-missed-a-crowdfunded-mosquito-dissecting-malaria-killig-robot/.

[5] -----, "SporoBot—Build a Robot. Fight Malaria. Save Lives! (YouTube video)": Sanaria, Inc, 2014, https://www.youtube.com/watch?feature=player_embedded&v=VblazNXcFGg.

[6] C. Borchers, "Robot may help fight malaria", The Boston Globe, May 8, 2014. http://www.bostonglobe.com/business/2014/05/07/mosquito-harvest/Qxto58qtpGHhRVfliT6aHI/story.html.

[7] Richie, T L, et al. "Progress with *Plasmodium falciparum* sporozoites (PfSPZ)-based malaria vaccines", *Vaccine* (2015) 33:7452-7461

What is claimed is:

1. A device configured for augmenting the extraction of salivary glands from a multiplicity of mosquitoes, each mosquito having a body, a neck, and a head, the device comprising:
a cartridge comprising a first end, and a second end opposite the first end and a front edge extending between the first end and second ends;
a multiplicity of slots having a given depth, the slots positioned between the first end and the second end, wherein an axis of the slots is disposed perpendicular to the front edge, wherein each slot further comprises an open leading end proximate to the front edge and an open trailing end distal from the front edge, wherein each of the cartridge slots is structurally configured to receive one of the multiplicity of mosquitoes such that the multiplicity of mosquitoes can be positioned in parallel with one another, and such that each is disposed in one of the multiplicity of slots within the cartridge such that the head of each mosquito is positioned to protrude beyond the front edge;
a cutting assembly coupled to the cartridge and comprising a movable blade extending between the first end and the second end of the cartridge and configured such that the blade moves along the front edge of the cartridge to separate the heads from the bodies of the multiplicity of mosquitoes;
a squeezer comprising a movable block extending between the first end and the second end of the cartridge, the block comprising fingers configured to extend between each of the cartridge slots, respectively, such that the block is configured to be pressed upon the bodies of the multiplicity of mosquitoes, thereby extruding mosquito salivary glands from the multiplicity of mosquito bodies; and
a means for collecting the salivary glands.

2. The device of claim 1 wherein the blade is movable with respect to necks of the multiplicity of mosquitoes positioned in the slots and configured such that the blade can be moved through the necks thereby separating the multiplicity of mosquito heads from the bodies.

3. The device of claim 1 wherein the slots are tapered at their leading ends such that the heads and necks of the mosquitoes pass through the leading ends of the slots, and such that the mosquito bodies are constrained within the slots.

4. The device of claim 1 wherein the blade is serrate comprising a multiplicity of notches positioned such that the notches align with the cartridge slots and configured such that the heads and necks of the mosquitoes can pass through the blade notches and the mosquito bodies are constrained within the slots, and the blade further configured such that the blade can be moved relative to the cartridge severing the heads from the bodies of the mosquitoes.

5. The device of claim 4 comprising a second blade identically serrate to the first blade and immediately adjacent to the first blade, with the notches of the first and second blades aligned, and the first and second blades configured such that the first and second blades can be displaced relative to each other for severing the heads from the bodies of the mosquitoes.

6. The device of claim 1 further comprising a mosquito staging platform coupled to the cartridge and configured to receive a multiplicity of mosquitoes and from which mosquitoes can be moved into the cartridge slots.

7. The device of claim 6 wherein the cartridge is removably affixed to the mosquito staging platform.

8. The device of claim 7 wherein the cutting assembly is removably affixed to the cartridge.

9. The device of claim 8 wherein the squeezer is removably affixed to the cartridge.

10. The device of claim 1 wherein the depth of the slots is less than the average thickness of the multiplicity of mosquitoes.

11. The device of claim 1 wherein the means for collecting the salivary glands comprises a salivary gland receptacle that is removably affixed to the squeezer.

12. A device configured for extracting salivary glands from a multiplicity of mosquitoes, each mosquito having a body, a neck, and a head, the device comprising:

a rear base comprising a first base side, and a second base side opposite the first base side, and each side adapted to receive a slotted cartridge;

a cartridge with first and second sides, wherein a leading edge located between the first and second sides includes a multiplicity of slots having a given depth arranged between the first side and the second side of the cartridge, wherein an axis of the slots is perpendicular to the front edge of the cartridge, wherein each slot has an open leading end proximate to the front edge and an open trailing end distal from the front edge, wherein the cartridge is configured to receive the multiplicity of mosquitoes, such that the multiplicity of mosquitoes can be positioned in parallel with one another, and such that each is disposed in one of the multiplicity of slots within the cartridge such that the head and neck of each mosquito protrudes beyond the front edge; a front base with a first and second side and a rear edge therebetween;

a cutting assembly attached to and located at the rear edge of the front base, the cutting assembly comprising a first blade extending between the first side and the second side of the cartridge and located proximate to the rear edge of the front base, a second blade adjacent to the first blade and distal to the rear edge, wherein both blades are serrate comprising a multiplicity of notches positioned such that the notches of the two blades align with each other and with the cartridge slots and configured to receive the mosquitoes such that the mosquito heads pass beyond the cartridge slots, and the mosquito bodies are constrained within the slots, and the first blade further configured to move relative to the second blade and to the front and rear base, along the front edge of the cartridge, the movement thereby separating the heads from the bodies of the multiplicity of mosquitoes;

a platform for receiving the separated heads of the multiplicity of mosquitoes; and a movable body squeezer comprising fingers configured to fit within the cartridge slots and extending between the first end and the second end of the cartridge, and configured such that the squeezer can be operably pressed such that the fingers press upon the bodies of the multiplicity of mosquitoes, thereby extruding a multiplicity of mosquito salivary glands from the multiplicity of mosquito bodies.

13. The device of claim 12 wherein the front base is removably coupled to the platform for receiving the separated heads of the multiplicity of mosquitoes.

14. The device of claim 12, further comprising:

means for collecting and pooling the multiplicity of extruded salivary glands, wherein the collecting means comprises a suction tube.

* * * * *